(12) United States Patent
    Goepfrich et al.

(10) Patent No.:  US 12,642,951 B2
(45) Date of Patent:     Jun. 2, 2026

(54) SYSTEMS AND METHODS FOR ENDOLUMINAL DEVICE TREATMENT

(71) Applicant: W. L. Gore & Associates, Inc., Newark, DE (US)

(72) Inventors: James L. Goepfrich, Flagstaff, AZ (US); Thomas E. Kariniemi, Flagstaff, AZ (US); William D. Montgomery, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 631 days.

(21) Appl. No.: 17/424,818

(22) PCT Filed: Jan. 17, 2020

(86) PCT No.: PCT/US2020/014107
    § 371 (c)(1),
    (2) Date: Jul. 21, 2021

(87) PCT Pub. No.: WO2020/154195
    PCT Pub. Date: Jul. 30, 2020

(65) Prior Publication Data
    US 2022/0088362 A1      Mar. 24, 2022

Related U.S. Application Data

(60) Provisional application No. 62/794,825, filed on Jan. 21, 2019.

(51) Int. Cl.
    *A61M 39/06*        (2006.01)
    *A61M 25/06*        (2006.01)

(52) U.S. Cl.
    CPC .... *A61M 39/0613* (2013.01); *A61M 25/0662* (2013.01); *A61M 2039/062* (2013.01);
    (Continued)

(58) Field of Classification Search
    CPC .......... A61M 39/0613; A61M 25/0662; A61M 2039/062; A61M 2039/0626;
    (Continued)

(56) References Cited

U.S. PATENT DOCUMENTS 2,982,511 A    5/1961  Connor
4,701,160 A    10/1987 Lindsay et al.
        (Continued)

FOREIGN PATENT DOCUMENTS

CN      104870045 A      8/2015
EP      1199051 B1       5/2006
        (Continued)

OTHER PUBLICATIONS

International Search Report and Written Opinion received for PCT Patent Application No. PCT/US2020/014107, mailed on May 20, 2020, 18 pages.
        (Continued)

*Primary Examiner* — Michael J Tsai
*Assistant Examiner* — Kathleen Paige Farrell

(57)              ABSTRACT

Various concepts relate to treatment systems for medical devices delivered into patients in medical procedures. The treatment system may include a proximal valve configured to receive the endoluminal device, an optional distal valve configured to receive the endoluminal device, and a treatment chamber configured to receive a portion of the endoluminal device.

27 Claims, 25 Drawing Sheets

(52) U.S. Cl.
CPC .............. *A61M 2039/0673* (2013.01); *A61M 2205/0216* (2013.01)

(58) Field of Classification Search
CPC .... A61M 25/00; A61M 29/00; A61M 39/225; A61M 2039/0686; A61M 5/36; A61M 2005/1403; A61M 25/0111; A61M 2039/0673; A61M 39/228; A61M 2205/0216; A61M 2039/0009; A61M 2039/0633; A61M 39/06; A61M 25/0097; A61M 39/0693; A61F 2/2427; A61F 2/966; A61F 2/07; A61F 2/95; A61F 2/9522; A61F 2/011; A61F 2/013; A61F 2/2436; A61F 2/962; A61F 2/954; A61F 2/0095; A61F 2/9517; A61B 17/3498; A61B 17/12118; A61B 90/70
See application file for complete search history.

(56) References Cited

U.S. PATENT DOCUMENTS

| | | | |
|---|---|---|---|
| 5,071,411 A | 12/1991 | Hillstead | |
| 5,238,984 A | 8/1993 | Wallquist et al. | |
| 5,329,921 A | 7/1994 | Socaris et al. | |
| 5,389,080 A | 2/1995 | Yoon | |
| 5,634,911 A | 6/1997 | Hermann et al. | |
| 5,740,810 A * | 4/1998 | Johnson ............... | A61B 5/0215 |
| | | | 251/117 |
| 6,138,984 A | 10/2000 | Abell | |
| 6,488,653 B1 | 12/2002 | Lombardo | |
| 6,676,639 B1 | 1/2004 | Ternstroem | |
| 7,049,380 B1 | 5/2006 | Chang et al. | |
| 7,390,317 B2 | 6/2008 | Taylor et al. | |
| 7,726,315 B2 | 6/2010 | Field | |
| 8,079,986 B2 | 12/2011 | Taylor et al. | |
| 8,177,806 B2 | 5/2012 | Chin et al. | |
| 8,231,604 B2 | 7/2012 | Devellian et al. | |
| 8,480,627 B2 | 7/2013 | Christiansen | |
| 8,882,745 B2 | 11/2014 | Devellian et al. | |
| 8,956,389 B2 | 2/2015 | Van Orden | |
| 9,078,981 B2 | 7/2015 | Subramaniam et al. | |
| 9,314,605 B2 | 4/2016 | Arcaro et al. | |
| 9,333,077 B2 | 5/2016 | Peter | |
| 9,498,364 B2 | 11/2016 | Costello | |
| 9,555,219 B2 | 1/2017 | Crisostomo et al. | |
| 9,592,143 B2 | 3/2017 | Shaw | |
| 10,010,411 B2 | 7/2018 | Peter | |
| 10,155,104 B2 | 12/2018 | Arcaro et al. | |
| 10,213,224 B2 | 2/2019 | Guggenheimer et al. | |
| 10,278,847 B2 | 5/2019 | Kölbel | |
| 10,314,667 B2 | 6/2019 | Garvey et al. | |
| 10,500,360 B1 | 12/2019 | Zachar | |
| 10,729,880 B2 | 8/2020 | Kim et al. | |
| 10,729,891 B2 | 8/2020 | Werneth et al. | |
| 10,751,485 B2 | 8/2020 | Von Oepen et al. | |
| 10,987,218 B2 | 4/2021 | Arcaro et al. | |
| 11,135,077 B2 | 10/2021 | Kratzberg et al. | |
| 2001/0021825 A1 | 9/2001 | Becker et al. | |
| 2005/0027306 A1 | 2/2005 | Krivoruchko et al. | |
| 2005/0149097 A1 | 7/2005 | Regnell et al. | |
| 2005/0171479 A1 | 8/2005 | Hruska et al. | |
| 2005/0261630 A1 | 11/2005 | Mottola et al. | |
| 2007/0012624 A1 | 1/2007 | Bacino et al. | |
| 2007/0100412 A1 * | 5/2007 | Dwyer et al. ..... | A61M 25/0122 |
| 2007/0168014 A1 | 7/2007 | Jimenez et al. | |
| 2008/0053892 A1 | 3/2008 | Bacino et al. | |
| 2008/0109028 A1 | 5/2008 | Styrc | |
| 2009/0234320 A1 | 9/2009 | Watson | |
| 2009/0270838 A1 * | 10/2009 | Berthiaume ............... | A61F 2/95 |
| | | | 604/524 |
| 2009/0306598 A1 * | 12/2009 | Arcaro ............... | A61M 39/228 |
| | | | 604/167.03 |
| 2010/0010442 A1 | 1/2010 | Shivkumar et al. | |
| 2011/0061229 A1 | 3/2011 | Vorderbrueck et al. | |

| | | | |
|---|---|---|---|
| 2015/0343179 A1 | 12/2015 | Schumacher et al. | |
| 2016/0198725 A1 | 7/2016 | Gunari et al. | |
| 2016/0220363 A1 * | 8/2016 | Peter ..................... | A61F 2/2415 |
| 2016/0346517 A1 * | 12/2016 | Werneth .................. | A61M 5/36 |
| 2016/0354598 A1 | 12/2016 | Arcaro et al. | |
| 2016/0376063 A1 * | 12/2016 | Salahieh ............... | A61F 2/2427 |
| | | | 206/210 |
| 2017/0143446 A1 * | 5/2017 | Kölbel .................. | B08B 9/0328 |
| 2017/0281382 A1 | 10/2017 | Lostetter et al. | |
| 2017/0367861 A1 | 12/2017 | Kolbel | |
| 2019/0030282 A1 * | 1/2019 | White ............... | A61M 25/1011 |
| 2019/0111246 A1 | 4/2019 | Arcaro et al. | |
| 2019/0125534 A1 | 5/2019 | Arcaro et al. | |
| 2020/0261250 A1 | 8/2020 | Bradway | |
| 2020/0282153 A1 | 9/2020 | Lam et al. | |
| 2021/0138201 A1 | 5/2021 | Schumacher et al. | |
| 2021/0187269 A1 | 6/2021 | Arcaro et al. | |
| 2021/0196929 A1 * | 7/2021 | Kenny ................... | A61F 2/966 |
| 2021/0402139 A1 | 12/2021 | Moisa et al. | |
| 2024/0341987 A1 | 10/2024 | Kariniemi et al. | |

FOREIGN PATENT DOCUMENTS

| | | | |
|---|---|---|---|
| EP | 3367978 B1 | 1/2020 | |
| GB | 0154019 A | 11/1920 | |
| GB | 1514019 A | 6/1978 | |
| JP | 45-037705 B1 | 11/1970 | |
| JP | 62-292170 A | 12/1987 | |
| JP | 2002-537953 A | 11/2002 | |
| JP | 2007-513707 A | 5/2007 | |
| JP | 2011-512468 A | 4/2011 | |
| JP | 2011-522589 A | 8/2011 | |
| JP | 2015-107635 A | 6/2015 | |
| JP | 2017-092813 A | 5/2017 | |
| JP | 2018-146441 A | 9/2018 | |
| WO | 99/11308 A1 | 3/1999 | |
| WO | 2004/045386 A2 | 6/2004 | |
| WO | 2004/093937 A2 | 11/2004 | |
| WO | 2008/021006 A2 | 2/2008 | |
| WO | 2008/045761 A2 | 4/2008 | |
| WO | 2009/148577 A1 | 12/2009 | |
| WO | 2016/183495 A2 | 11/2016 | |
| WO | 2020/154195 A1 | 7/2020 | |
| WO | 2020/247384 A1 | 12/2020 | |
| WO | 2021/037917 A1 | 3/2021 | |

OTHER PUBLICATIONS

Grover et al., "Cerebral embolic protection in thoracic endovascular aortic repair", Journal of Vascular Surgery, vol. 68, No. 6, Dec. 2018, pp. 1-11.

Inci et al., "Air bubbles are released by thoracic endograft deployment: An in vitro experimental study", SAGE Open Medicine, vol. 4, No. 1, Nov. 9, 2016, pp. 1-5.

International Search Report and Written Opinion received for PCT Patent Application No. PCT/US2024/024955, mailed on Sep. 2, 2024, 16 pages.

Johnson et al., "Upper Extremity Arterial Access During Endovascular Aortic Repair", Journal of Vascular Surgery, vol. 65, No. 6, pp. 1.

Milsom et al., "A Dual-Vent Left Heart Deairing Technique Markedly Reduces Carotid Artery Microemboli", Ann Thorac Surg, vol. 66, No. 1, 1998, pp. 785-791.

Perera et al., "Cerebral embolization, silent cerebral infarction and neurocognitive decline after thoracic endovascular aortic repair",BJS, vol. 105, No. 1, 2018, pp. 366-378.

Rohlffs et al., "Air Embolism During TEVAR: Carbon Dioxide Flushing Decreases the Amount of Gas Released From Thoracic Stent-Grafts During Deployment", Journal of Endovascular Therapy, vol. 24, No. 1, 2017, pp. 84-88.

Taylor et al., "Cerebral Microemboli During Cardiopulmonary Bypass: Increased Emboli During Perfusionist Interventions", Ann Thorac Surg, vol. 68, No. 1, 1999, pp. 89-93.

(56)  References Cited

OTHER PUBLICATIONS

Willcox et al., "Venous Air in the Bypass Circuit: A Source of Arterial Line Emboli Exacerbated by Vacuum-Assisted Drainage", Ann Thorac Surg, vol. 68, No. 1, 1999, pp. 1285-1289.

* cited by examiner

SYSTEMS AND METHODS FOR ENDOLUMINAL DEVICE TREATMENT

CROSS-REFERENCE TO RELATED APPLICATION

This application is a national phase application of PCT Application No. PCT/US2020/014107, internationally filed on Jan. 17, 2020, which claims the benefit of U.S. Provisional Application No. 62/794,825, filed Jan. 21, 2019, both of which are herein incorporated by reference in their entireties for all purposes.

FIELD

The disclosure relates generally to introducer systems and methods for treatment of devices introduced into a body of a patient, and more specifically systems and methods for endoluminal device treatment.

BACKGROUND

Endoluminal devices are commonly delivered into the body of a patient (e.g., into the patient's vasculature) using an introducer system. Introducer systems typically include valves or similar features to stop backflow of body fluids (e.g., blood) through to the introducer while permitting the endoluminal device to pass through the introducer and into the patient's body. In various instances, a clinician or other user of an endoluminal device may also wish to perform one or more treatments on the endoluminal device.

Particularly advantageous introducer systems include those sold by W. L. Gore & Associates, Inc. under the tradename GORE® DrySeal Flex Introducer Sheath. GORE® DrySeal Flex Introducer Sheaths are intended to be inserted in the vasculature to provide conduits for insertion of endovascular devices while minimizing blood loss associated with such insertions. The GORE® systems include an introducer sheath with the GORE® DrySeal Valve attached, a twist style locking dilator, and a syringe. The introducer sheath is a composite tube which consists of a flat stainless steel wire reinforced hydrophilic coated Pebax® outer tube and PTFE liner with a tapered leading tip. The introducer sheath is attached to the GORE® DrySeal Valve. The GORE® DrySeal Valve includes an outer silicone tube and an inner film tube. The region between the silicone tube and film tube can be pressurized by injecting saline into the region using a syringe. Additional examples of similar systems can be found in U.S. Pat. No. 10,155,104, "Valve Assembly for Medical Procedures," filed by W. L. Gore & Associates, Inc.

SUMMARY

Various examples relate to systems used for treating endoluminal devices, as well the methods used to treat such devices, whether those methods use existing device technology with improved methodology or use improved systems. While most examples are provided in the context of endoluminal devices, and more particularly implantable devices that are delivered through the vasculature, the principles and examples of this disclosure are meant to apply broadly to any device that is treated as part of introduction into the body using an introducer system. It will also be apparent that various advantages may be achieved using the systems and methodologies described herein, including removal of entrapped air, pre-wetting or pre-medicament of one or more portions of an endoluminal device, and other treatments that may be implemented to facilitate improved clinical results.

According to one example ("Example 1"), a treatment system for an endoluminal device includes a proximal valve, optionally, a distal valve, and a treatment chamber. The proximal valve may be configured to receive the endoluminal device, the proximal valve including a proximal seal mechanism actuatable between a sealed state and an unsealed state to seal around the endoluminal device. Where present, the distal valve may be configured to receive the endoluminal device, the distal valve including a distal seal mechanism actuatable between a sealed state and an unsealed state around the endoluminal device. The treatment chamber may be configured to receive a portion of the endoluminal device, such as a portion that extends between the proximal valve and the distal valve. The treatment chamber is fluidly coupled to the proximal valve to define a treatment space. The treatment chamber is optionally coupled between the proximal valve and the distal valve to define the treatment space between the proximal valve and the distal valve.

According to another example further to Example 1 ("Example 2"), one or both of the proximal seal mechanism and the distal seal mechanism includes an outer tube, an inner tube, and a pressurizable space formed between an inner surface of the outer tube and an outer surface of the inner tube, and the pressurizable space being pressurizable to cause the inner tube to conform around the endoluminal device to form a seal around the endoluminal device.

According to another example further to Example 2 ("Example 3"), the inner tube is formed of a conformable material.

According to another example further to Example 3 ("Example 4"), the conformable material includes one or more of ePTFE (expanded polytetrafluoroethylene), silk, and Poly-paraphenylene terephthalamide.

According to another example further to any one of Examples 2 to 4 ("Example 5"), the outer tube is formed of an elastomeric material.

According to another example further to Example 5 ("Example 6"), the elastomeric material includes silicone.

According to another example further to any preceding Example ("Example 7"), the system further includes an introducer sheath extending distally from the distal valve.

According to another example further to any preceding Example ("Example 8"), the treatment chamber has a proximal portion adjacent the proximal valve, a distal portion adjacent the distal valve, the treatment system further comprising a proximal treatment port in fluid communication with the proximal portion of the treatment chamber and a distal treatment port in fluid communication with the distal portion of the treatment chamber.

According to another example further to Example 8 ("Example 9"), each of the proximal and distal treatment ports includes a valve for fluidly sealing and unsealing the proximal and distal treatment portions, respectively.

According to another example further to any preceding Example ("Example 10"), the endoluminal device is a transcatheter delivery system including a catheter and an implantable device maintained at a compacted, delivery diameter or state, and further wherein the treatment chamber is configured to receive the implantable device at the compacted, delivery diameter or state.

According to another example further to any preceding Example ("Example 11"), the endoluminal device is a transcatheter delivery system including a catheter and an implantable device maintained at a compacted, delivery diameter or state by the delivery catheter, and further wherein the treatment chamber is configured to receive the implantable device at an intermediate, partially expanded diameter that is greater than the compacted, delivery diameter.

According to another example ("Example 12"), a method of treating an endoluminal device for introduction into a body of a patient includes positioning the endoluminal device into a treatment system, the treatment system including a proximal valve, a distal valve, and a treatment chamber defining a treatment space between the proximal valve and the distal valve, the endoluminal device including a first portion extending through the proximal valve, a second portion extending through the distal valve, and a treatment portion extending through the treatment space of the treatment chamber. The method also includes closing the proximal and distal valves to seal the proximal valve against the first portion of the endoluminal device and the distal valve against the second portion of the endoluminal device. And, the method includes delivering a treatment medium into the treatment space to expose the treatment portion of the endoluminal device to the treatment medium.

According to another example further to Example 12 ("Example 13"), the treatment portion of the endoluminal device includes an implantable device maintained by a delivery catheter.

According to another example further to Examples 12 or 13 ("Example 14"), the treatment portion of the endoluminal device includes a proximal portion of an implantable device and a distal portion of the endoluminal device extends from the distal valve.

According to another example further to any one of Examples 12 to 14 ("Example 15"), the treatment medium is selected from one or more of saline, carbon dioxide, perfluorocarbon solution, methylene blue, and combinations thereof.

According to another example further to any one of Examples 12 to 15 ("Example 16"), delivering the treatment medium into the treatment space forces air from the treatment portion of the endoluminal device.

According to another example further to any one of Examples 12 to 16 ("Example 17"), the method further includes delivering the treatment medium into the treatment space through at least one of a proximal treatment port in fluid communication with a proximal portion of the treatment chamber, and a distal treatment port in fluid communication with a distal portion of the treatment chamber.

According to another example further to any one of Examples 12 to 17 ("Example 18"), the treatment medium exits the treatment chamber through a distal treatment port in fluid communication with a distal portion of the treatment chamber.

According to another example further to any one of Examples 12 to 18 ("Example 19"), the endoluminal device includes a sleeve maintaining an implantable device in a compacted, delivery state, and further wherein the distal valve is closed over the sleeve and the treatment medium exits the treatment chamber from the distal valve through one or more gaps between the sleeve and the implantable device.

According to another example further to any one of Examples 12 to 19 ("Example 20"), the treatment system includes an introducer sheath, and the method further comprises inserting the introducer sheath into a body lumen of the patient.

According to another example further to Examples 20 ("Example 21"), the treatment medium is delivered into the treatment space with the introducer sheath inserted into the body lumen of the patient.

According to another example ("Example 22"), a method of treating an endoluminal device for introduction into a body of a patient includes positioning the endoluminal device into a treatment system, the treatment system including a valve and a treatment chamber extending from the valve and the endoluminal device including a first portion extending through the valve and a treatment portion extending into the treatment space of the treatment chamber. The method also includes closing the valve to seal the valve against the first portion of the endoluminal device and sealing the treatment chamber. The method may also include delivering a treatment medium into a treatment space within the treatment chamber to expose the treatment portion of the endoluminal device to the treatment medium.

According to another example further to Example 22 ("Example 23"), the treatment chamber is sealed with a cap member extending distally from the valve.

According to another example further to Example 22 ("Example 24"), the treatment chamber is sealed manually with a cap member.

According to another example further to Example 24 ("Example 25"), the treatment chamber is sealed digitally by a user of the treatment system.

According to another example further to any one of Examples 22 to 25 ("Example 26"), the endoluminal device includes a sleeve maintaining an implantable device in a compacted, delivery state, and further wherein the valve is closed over the sleeve and the treatment medium exits the treatment chamber through the valve through one or more gaps between the sleeve and the implantable device.

According to another example ("Example 27"), a treatment system for an endoluminal device includes a proximal valve and a treatment chamber. The proximal valve may be configured to receive the endoluminal device, the proximal valve including a proximal seal mechanism actuatable between a sealed state and an unsealed state to seal around the endoluminal device. The treatment chamber may be configured to receive a portion of an endoluminal device, the treatment chamber being fluidly coupled to the proximal valve. The treatment chamber may have a proximal portion fluidly coupled to the proximal valve and a distal portion that is fluid-tight or otherwise sealed (e.g., permanently or using a removable sealing mechanism, such as a removable cap member).

According to another example further to Example 27 ("Example 28"), the distal portion of the treatment chamber is sealed with a cap member extending distally from the valve.

According to another example further to Example 27 ("Example 29"), the distal portion of the treatment chamber is sealed by a clamp member.

According to another example further to Example 27 ("Example 30"), the distal portion of the treatment chamber is sealed by a plug.

According to another example further to any one of Examples 27 to 30 ("Example 31"), the endoluminal device is received in the treatment chamber, the endoluminal device including a sleeve maintaining an implantable device in a compacted, delivery state, and further wherein the proximal valve is closed over the sleeve and a pressurized treatment medium is present in the treatment chamber.

According to another example further to Examples 27 or 31 ("Example 32"), the treatment system further comprises a distal valve including a distal seal mechanism actuatable between a sealed state and an unsealed state to seal around the endoluminal device and an introducer sheath removably coupled to the distal valve.

According to another example, further to Example 32 ("Example 33"), the introducer sheath includes a hemostatic valve removably coupled to the distal valve.

According to another example, further to any preceding Example ("Example 34"), the treatment chamber (e.g., distal sheath) is configured to be adjustable in length, the treatment chamber including one or more of the following: one or more removable sections (e.g., releasably or breakably coupled), one or more longitudinally splittable features, a configuration that is longitudinally compressible (e.g., to define or otherwise include a plurality of creases, folds, or pleats similar to the bellows of an accordion), and/or a configuration to extend or retract in length upon imparting a twisting force to the treatment chamber (e.g., where the treatment chamber includes a helical wrap, or layered assembly that, while sealed, may be twisted to cause relative movement of the helical wrap or layers to reduce or extend the length of the treatment chamber).

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Figures 1A, 1B:
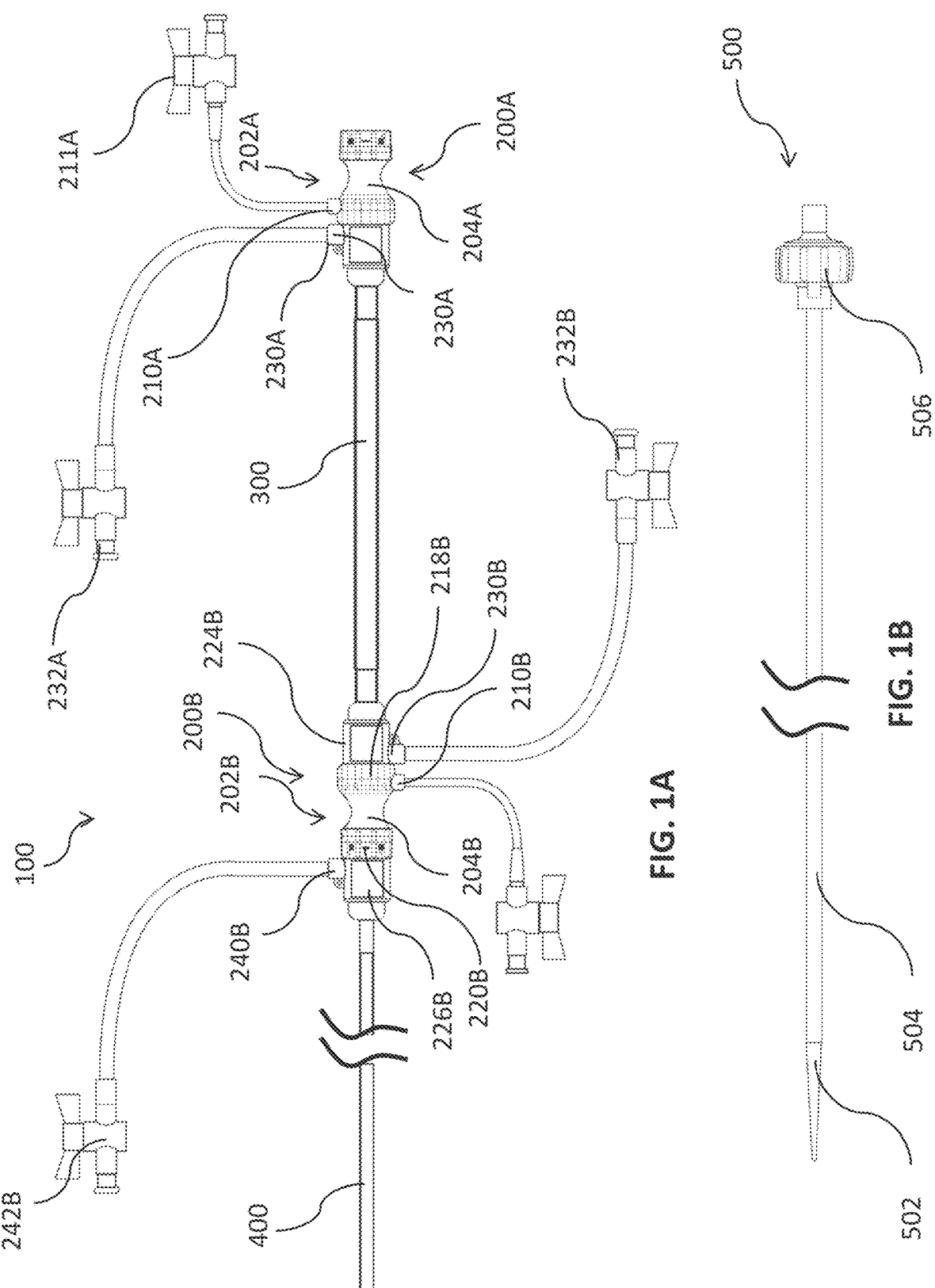
FIG. 1A shows a treatment system, according to some embodiments.
FIG. 1B shows a dilator tool for use with a treatment system such as that shown in FIG. 1A, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

This disclosure is not meant to be read in a restrictive manner. For example, the terminology used in the application should be read broadly in the context of the meaning those in the field would attribute such terminology.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

Various examples are provided of treatment systems with features facilitating treatment of endoluminal devices before, during, or after introduction of the endoluminal devices into the body of a patient, as well as methods of endoluminal device treatment. In various examples, a treatment medium is applied to the endoluminal device, and specifically an implantable device of the endoluminal device, to remove entrapped air or otherwise pre-treat the implantable device for reduced risk of emboli, or other deleterious effects. It has been found that saline is an effective treatment medium, and also that carbon dioxide is an effective treatment medium, among others. Entrapped carbon dioxide that has displaced previously entrapped air is generally preferable as carbon dioxide exhibits smaller "bubbles" when released in the blood stream and thus exhibit reduced physiologic impact. While some examples of features and advantages have been described above, additional or alternative features and advantages are contemplated according to the instant disclosure.

FIG. 1A shows a treatment system 100 configured as, or integrated with an introducer system, according to some examples. As shown, the treatment system 100 includes a proximal valve 200A, a distal valve 200B, a treatment chamber 300 (which may also be referred to as a garage conduit), and a distal sheath 400. In general terms, the treatment system 100 includes an inner lumen 101 (FIG. 3) that extends continuously through the full length of the treatment system 100, including through the proximal valve 200A, the treatment chamber 300, the distal valve 200B, and the distal sheath 400 configured to facilitate introduction of an endoluminal device into a body lumen. Thus, the treatment system 100 may be used to introduce an endoluminal device into a body of a patient (not shown) by passing an endoluminal device through the inner lumen 101 from a location external to a body of a patient to a location inside the patient. The treatment system 100 may be utilized with a variety of endoluminal devices, such as those illustrated in FIGS. 1B and 6 to 9. In various examples, the treatment system 100 is used to treat the endoluminal device (e.g., flush air from a portion of the endoluminal device) with a treatment medium (e.g., carbon dioxide, saline, perfluorocarbon solution, methylene blue, or others).

FIG. 1B shows an optional dilator 500 that can be used in combination with the treatment system 100 to access one or more body lumens of a patient. In use, the dilator 500 is received through the inner lumen 101 of the treatment system 100 and is utilized in association with the treatment system 100 to gain access to a patient's body (e.g., vasculature, airways, biliary tract, gastrointestinal tract, cardiac spaces, or others). The various valves of the treatment system 100 assist in preventing back bleeding through the treatment system 100 during a dilation procedure using the dilator 500. As shown, the dilator 500 includes a dilator tip 502, a dilator body 504 and a hub end 506. The hub end 506 is configured to connect with a proximal portion of the treatment system 100 and can also help prevent backout of the dilator 500 during insertion of the dilator 500 into the patient's body.

Figure 3:
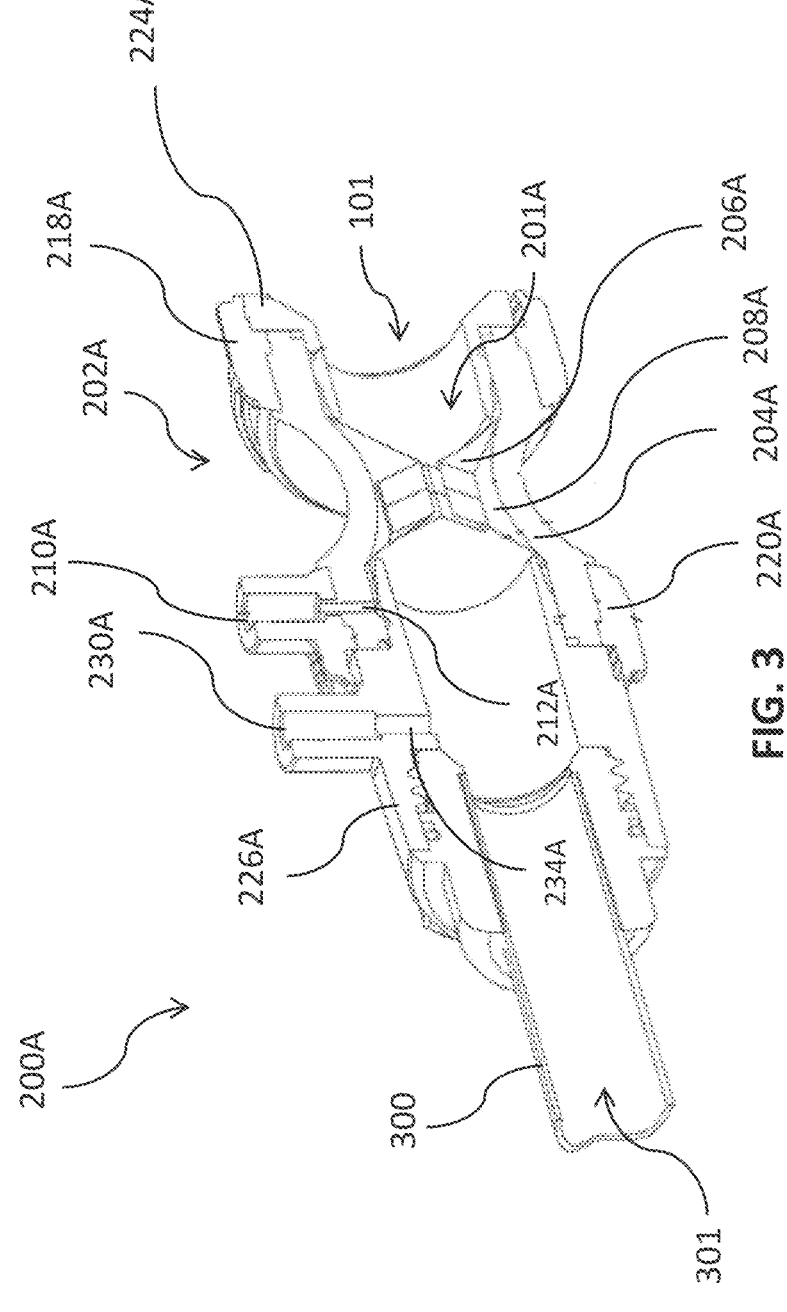
FIG. 3 is a cut-away view of a proximal valve of the treatment system of FIG. 1A, according to some embodiments.

FIG. 3 is an enlarged, partial cut-away view of a proximal portion of the treatment system 100 showing various features of the proximal valve 200A in an assembled state. FIG.

Figure 5:
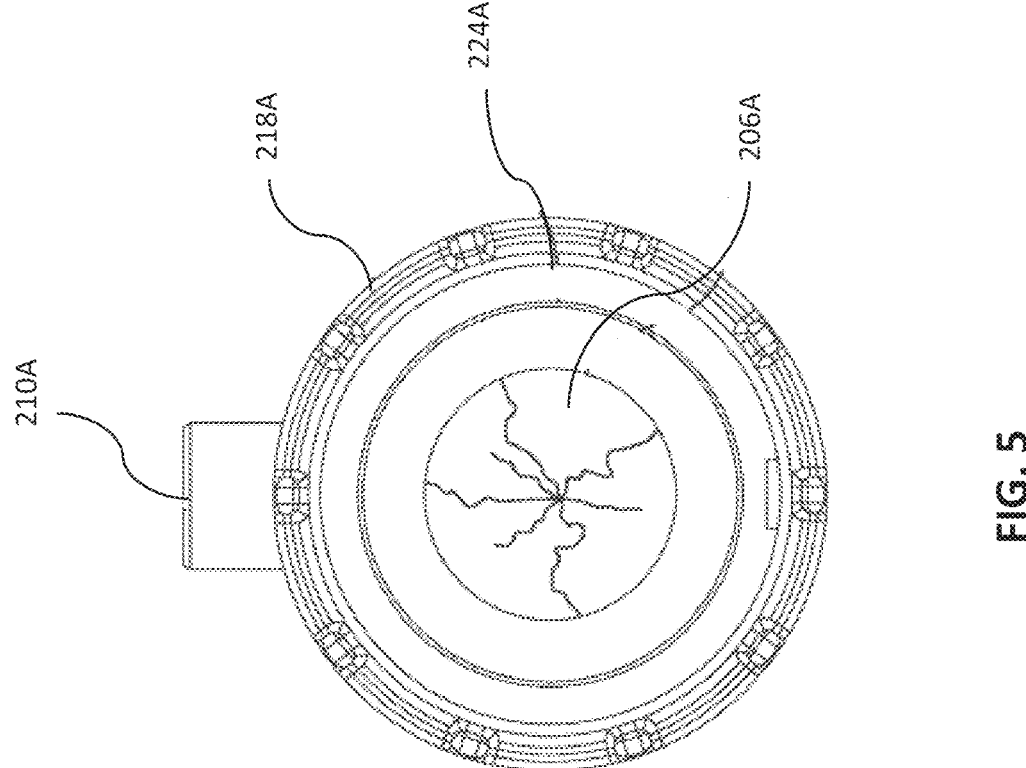
FIG. 5 is an end view of the proximal valve of FIG. 3 in a pressurized, closed state, according to some embodiments.

4 is an isometric view of the same portion of the treatment system 100 as FIG. 3, but in a disassembled state. FIG. 5 is an end view of the treatment system 100 showing the proximal valve 200A in a pressurized, and sealed state according to some examples.

The proximal valve 200A is generally configured to receive an endoluminal device (e.g., dilator, endovascular delivery systems, balloon catheters, percutaneous delivery systems, and the like) and provide a fluid seal around the outer surface of the endoluminal device to prevent unwanted backflow (e.g., of blood and/or a treatment medium) around the endoluminal device and back through the inner lumen 101 of the treatment system 100. Additionally, the proximal valve 200A is configured to fully close, or close off and seal with itself to a closed, or sealed state when no endoluminal device is present (e.g., as shown in FIG. 5). Again, this prevents unwanted backflow (e.g., of blood and/or a treatment medium) through the proximal valve 200A. Suitable examples of designs, materials, and methods of making the proximal valve 200A, as well as the distal valve 200B (which is similar to the proximal valve 200A) and distal sheath 400 may be found in U.S. Pat. No. 10,155,104, entitled "Valve Assembly for Medical Procedures," although a variety of designs, materials and methods of making such valves are contemplated.

As can be seen in FIG. 3, the proximal valve 200A has an inner lumen 201A that extends the length of the proximal valve 200A. As previously referenced, the inner lumen 201A of the proximal valve 200A forms a portion of the inner lumen 101 of the treatment system 100. The proximal valve 200A includes a proximal seal mechanism 202A that is actuatable between a sealed state and an unsealed state to open and close, or dilate, a portion of the inner lumen 201A. The proximal seal mechanism 202A includes an outer tube 204A, an inner tube 206A, a pressurizable space 208A (FIG. 3) formed between an inner surface of the outer tube 204A and an outer surface of the inner tube 206A, and a fill port 210A. Though apparent from the figures, it is noted that the pressurizable space 208A is generally sealed off apart from the access provided by the fill port 210A according to various examples. As illustrated, the proximal seal mechanism 202A also includes a rear ring 218A and a front ring 220A secured in an opposing manner toward either end of the outer tube 204A. The rings generally assist with supporting, sealing, and coupling the proximal seal mechanism 202A with a remainder of the proximal valve 200A.

The proximal valve 200A also includes a rear fitting 224A attached to the rear ring 218A and a front fitting 226A attached to the front ring 220A (e.g., via complementary threads, adhesives, snap fits, fasteners and/or other mechanisms). The rear and front fittings 224A, 226A can help to secure the various portions of the proximal valve 200A together in a sealed manner and may also provide a mechanism or manner for securing the proximal valve 200A to other components of the treatment system 100, such as the treatment chamber 300. The rear fitting 224A may also be configured to be coupled to one or more portions of an endoluminal device, such as the hub end 506 (FIG. 1B).

In addition to the fill port 210A, the proximal valve 200A also has a treatment port 230A (also described as a flush port) in fluid communication with the inner lumen 201A of the proximal valve 200A at a location distal to the proximal seal mechanism 202A. As will be subsequently described, the treatment port 230A may be utilized to deliver a treatment medium into the treatment chamber 300.

In some embodiments, the outer tube 204A has an hourglass shape in a relaxed state, although right cylinder and other shapes are contemplated. The outer tube 204A may have elastic properties (e.g., being formed of an elastomeric material) and distend (physically expand) upon pressurization of the pressurizable space 208A to deflect radially outward from the hourglass shape to a more cylindrical state and potentially a more bulbous, outwardly convex shape. In some examples, the outer tube 305A is formed of a silicone material (e.g., using insertion molding techniques), although a variety of materials including any of a variety of elastomeric materials or materials having elastic properties are contemplated. For example, the outer tube 204A may be constructed of any elastomer, latex or polycarbonate with desirable mechanical and biocompatible properties.

The expansion characteristic of the outer tube 204A can provide a visual indicator that the pressurizable space 208A has been positively pressurized, and thus the proximal valve 200A has been closed. In some examples, when the proximal seal mechanism 202A is positively pressurized and closed, the hourglass shape of outer tube 204A becomes distended to indicate a desirable positive pressure in the pressurizable space 208A (e.g., one that will sufficiently prevent backflow through the proximal seal mechanism 202A).

The inner tube 206A may be constructed of any thin, strong, drapeable material such as ePTFE, fabrics, silk, or Kevlar® brand fiber, for example. Such materials may be used as a single layer construct or a multi-layer construct as appropriate. As shown, the inner tube 206A may have an hourglass shape in a relaxed state. The shape of the inner tube 206A, can be varied as desired, including wall thickness, length, width, diameter, and other features.

In use, the inner tube 206A is thin and conformable and as such, once the pressurizable space 208A is positively pressurized, the inner tube 206A is deflected inwardly and drapes, or closely conforms, to the outer perimeter of an endoluminal device received through the proximal valve 200A to form a seal. When no endoluminal device is present, the inner tube 206A deflects inwardly such that the inner surface of the inner tube 206A engages itself to form a seal.

As shown, the fill port 210A includes a coupling feature 211A associated with the front ring 220A and a passage 212A formed through the outer tube 204A into the pressurizable space 208A. The coupling feature 211A is optionally configured to be attached to a syringe (e.g., the coupling feature 211A can be configured as a valved luer fitting). Regardless of the particular pathway, the fill port 210A provides a means for pressurizing (or depressurizing) the pressurizable space 208A. In particular, the fill port 210A is in fluid communication with the pressurizable space 208A.

The fill port 210A can be configured to be coupled to any of a variety of positive or negative pressure sources (fluid or gas), including a syringe (not shown). For reference, the pressurizable space 208A may be filled with any suitable material or materials. For example, although saline solution may be preferred in certain applications, the pressurizable space 208A may be positively pressurized with one or more of: air, silicone, water, saline solution, low volatility biocompatible liquids, glycerin, propylene glycol, polyethylene glycol, compressible foam, elastomeric spheres, crosslinked silicone gels, and combinations thereof.

Regardless, a pressure source can be used to deliver a suitable material (e.g., saline solution) into the pressurizable space 208A (to positively pressurize) or to remove material from the pressurizable space 208A (to negatively pressurize, or depressurize), respectively, causing closing or opening, respectively, of the proximal seal mechanism 202A. In particular, according to various embodiments, upon positive pressurization of the pressurizable space 208A using the fill port 210A, the inner tube 206A collapses inwardly (e.g., against itself or around a device received through the inner tube 206A) to form a seal. FIG. 5 shows an end view of the treatment system 100 with the inner tube 206A of the proximal valve 200A collapsed and engaged with itself under positively pressurized conditions.

The front fitting 226A is secured to the front ring 220A as well as a proximal portion of the treatment chamber 300 (e.g., via complementary threading as shown in FIG. 3), and thus assists with fluidly coupling the proximal valve 200A to the treatment chamber 300. The front fitting 226A or portions thereof can be formed a clear material (e.g., transparent or translucent polymer) which can permit visual confirmation by a user of the treatment system 100 that a device (or portion thereof) being inserted through the treatment system 100 has passed through the proximal valve 200A, and in particular beyond the proximal seal mechanism 202A.

As shown, the treatment port 230A communicates with the inner lumen 201A at a location distal to the proximal seal mechanism 202A. The treatment port 230A includes a coupling feature 232A (e.g., a valved luer fitting for sealing and unsealing the treatment port 230A) and a passage 234A through the front fitting 226A into the inner lumen 201A of the proximal valve 200A (e.g., at a location distal to the proximal seal mechanism 202A as shown). Regardless of the particular pathway, the treatment port 230A provides a means for conveying a treatment medium into and/or out from the inner lumen 201A of the proximal valve 200A (and into or out from a proximal portion of the treatment chamber 300) as subsequently described.

Figure 4:
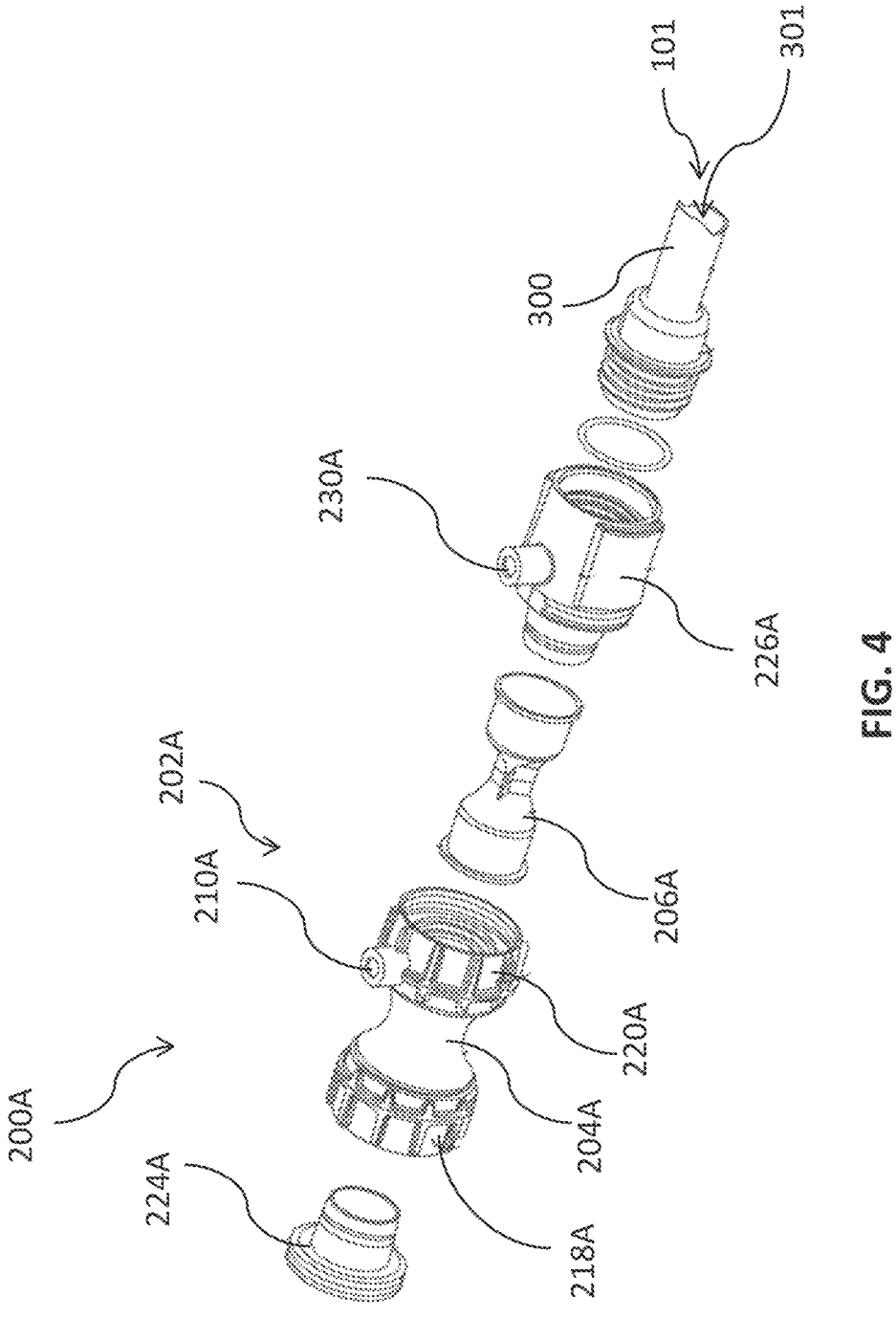
FIG. 4 is an isometric view of the proximal valve of FIG. 3 in a disassembled state, according to some embodiments.

As shown in one or more of FIGS. 1A, 3, and 4 the treatment chamber 300 has an inner lumen 301 that forms part of the inner lumen 101 of the treatment system 100. The treatment chamber 300 includes a proximal coupling 310, a distal coupling 312, and a body 314 extending between the proximal and distal couplings 310, 312. The proximal coupling 310 is configured to secure the treatment chamber 300 to the proximal valve 200A in a sealing manner (e.g., via complementary threads) and the distal coupling 312 is similarly configured to secure the treatment chamber 300 to the distal valve 200B in a sealing manner (e.g., via complementary threads). The body 314 is optionally hollow and tubular in configuration and is sized (e.g., of suitable cross-section and length) to receive a desired portion of an endoluminal device positioned between the proximal valve 200A and the distal valve 200B. In particular, the treatment chamber 300 is fluidly coupled between the proximal valve 200A and the distal valve 200B to define a treatment space with in the inner lumen 301 between the proximal valve 200A and the distal valve 200B. The treatment chamber 300 can be relatively rigid or relatively flexible as desired. In some examples the treatment chamber 300 or portions thereof are partially or fully transparent to permit viewing of an endoluminal device received in the treatment chamber 300.

As shown in FIG. 1A, the distal valve 200B can be substantially similar in form and function to the proximal valve 200A, according to various examples. As such, the features of the distal valve 200B can be described collectively with those of the proximal valve 200A. As shown in FIG. 1A, the proximal valve 200A and distal valve 200B are substantially similar (though the distal valve 200B has a modified rear fitting 224B, which is substantially similar to the front fitting 226A of the proximal valve 200A). Therefore, where features of the distal valve 200B that correspond to features of the proximal valve 200A are called out, the same reference numbers are used for each, except rather than being followed by an "A" corresponding features of the distal valve 200B are followed by a "B".

According to some embodiments, similarly to the proximal valve 200A, the distal valve 200B also has an inner lumen (not shown) that forms part of the inner lumen 101 of the treatment system 100. The distal valve 200B is also configured to receive an endoluminal device within the lumen of the distal valve 200B. And, the distal valve 200B also includes a distal seal mechanism 202B that is structured and operates similarly to the proximal seal mechanism 202A and is actuatable between a sealed state and an unsealed state to open and close, or dilate, a portion of the inner lumen of the distal valve 200B.

The distal seal mechanism 202B includes an outer tube 204B, an inner tube (not shown), a pressurizable space (not shown) formed between an inner surface of the outer tube 204B and an outer surface of the inner tube, and a fill port 210B. The pressurizable space is generally sealed off apart from the access provided by the fill port 210B, similar to various examples of the proximal seal mechanism 202A. As illustrated, the distal seal mechanism 202B also includes a rear ring 218A and a front ring 220B secured in an opposing manner toward either end of the outer tube 204B. The rings 218A, 218B generally assist with supporting, sealing, and coupling the distal seal mechanism 202B with a remainder of the distal valve 200B.

As shown, the distal valve 200B also includes a rear fitting 224B attached to the rear ring 218B and a front fitting 226B attached to the front ring 220B (e.g., via complementary threads, adhesives, snap fits, fasteners and/or other mechanisms). The rear and front fittings 224B, 226B can help to secure the various portions of the distal valve 200B together. As shown, the rear fitting 224B is effectively a mirror image of the front fitting 226B (as well as front fitting 226A). The rear fitting 224B provides a mechanism or manner for securing the proximal valve 200A to the treatment chamber 300 in a similar manner to the front fitting 226A of the proximal valve 200A (e.g., via complementary threads on each). The front fitting 226B of the distal valve 200B is, in turn, configured to be coupled to the distal sheath 400 (e.g., via complementary threads on each).

In addition to the fill port 210B for actuating the distal seal mechanism 202B, the distal valve 200B also optionally has a treatment port 230B (also described as a flush port) in fluid communication with the inner lumen 201A of the proximal valve 200A at a location proximal to the distal seal mechanism 202B. The treatment port 230B includes a coupling feature 232B (e.g., a valved, luer fitting for sealing and unsealing the treatment port 230A) associated with the rear fitting 224B and a passage (not shown) through the rear fitting 224B into the lumen of the distal valve 200B (e.g., at a location proximal to the distal seal mechanism 202B as shown). Regardless of the particular pathway, the treatment port 230B provides a means for conveying a treatment medium into and/or out from the inner lumen of the distal valve 200B (and into and/or from a distal portion of the treatment chamber 300). For example, as shown by the direction of the arrows in FIG. 10, the treatment medium enters the inner lumen from the first treatment port 230A, passes through the inner lumen through the treatment chamber 300, and exits the inner lumen from the second treatment port 230B.

Additionally, as shown, the distal valve 200B further includes a treatment port 240B (also described as a flush port) distal of the distal seal mechanism 202B in fluid communication with the inner lumen of the distal valve 200B. The treatment port 240B includes a coupling feature 242B (e.g., a valved, luer fitting for sealing and unsealing the treatment port 230A) associated with the front fitting 226B and a passage (not shown) through the front fitting 226B into the lumen of the distal valve 200B (e.g., at a location distal to the distal seal mechanism 202B as shown). Regardless of the particular pathway, the treatment port 240B provides a means for conveying a treatment medium into and/or out from the inner lumen of the distal valve 200B (and into and/or out from the distal sheath 400).

As shown in FIG. 1A, the distal sheath 400 is coupled to the front fitting 226B of the distal valve 200B (e.g., via complementary threading on the two components). The distal sheath 400 is substantially tubular and has an inner lumen (not shown) that forms a portion of the inner lumen 101 of the treatment system 100. The distal sheath 400 may be formed of a variety of materials, but in some examples is formed of fluorinated ethylene propylene (FEP), high-density polyethylene, and/or any other suitable material. The distal sheath 400 may be configured with an outer dimeter ranging between a variety of sizes, but in some examples is sized from 12 Fr to 26 Fr. The distal sheath 400 may have any of a variety of lengths as desired and may be configured for insertion into a body lumen (e.g., vasculature) of a patient to assist with the introduction of an endoluminal device into the patient (not shown).

Figures 2A, 2B:
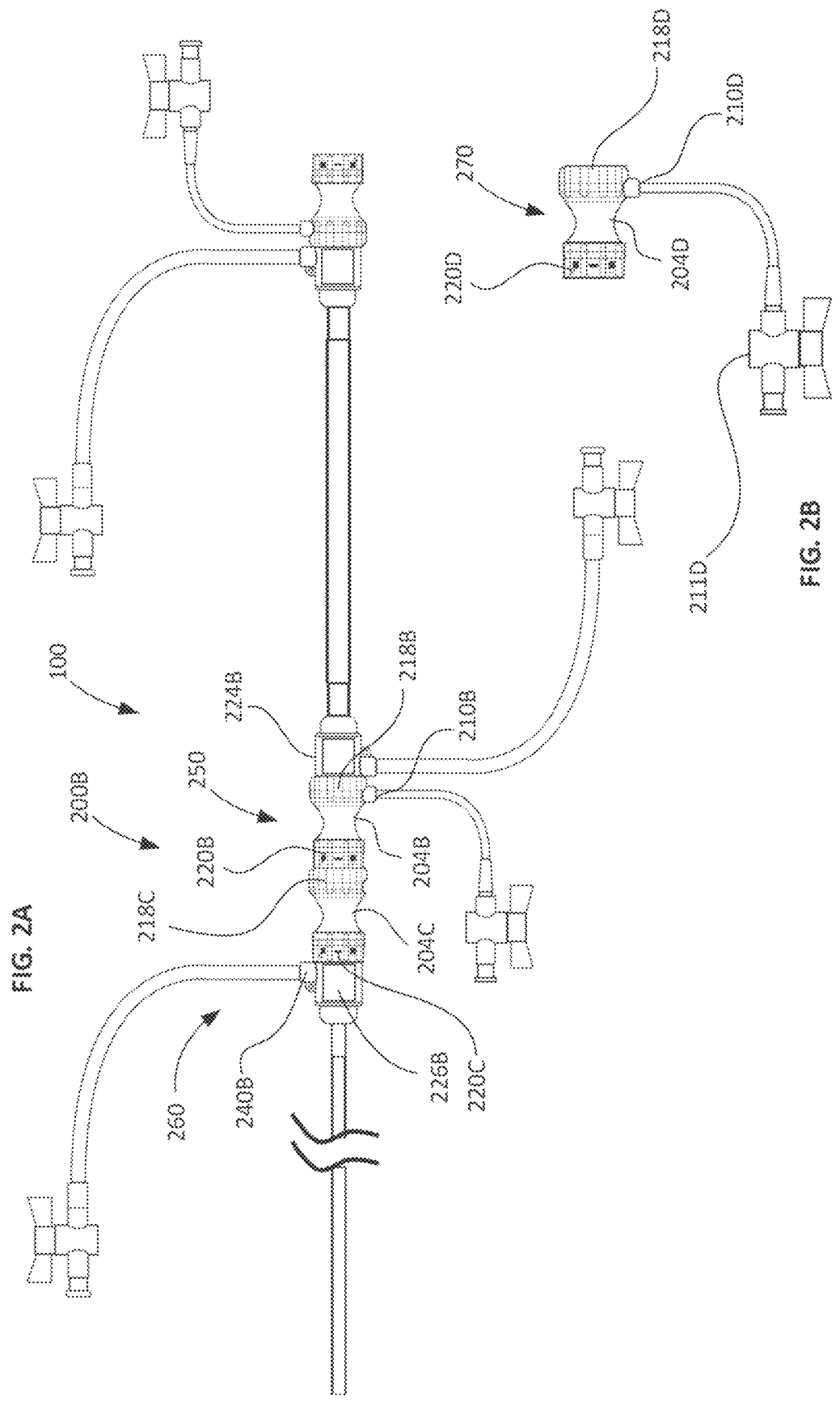
FIG. 2A shows a treatment system, according to some embodiments.
FIG. 2B shows an additional port connector implementable in the treatment system of FIG. 2A, according to some embodiments.

FIG. 2A shows another embodiment the treatment system 100, according to some examples. As shown, the distal valve 200B includes a fill port connector 250 and a treatment port connector 260. The fill port connector 250 fluidly connects the fill port 210B with the pressurizable space 208A to provide a means for pressurizing (or depressurizing) the pressurizable space 208A. The treatment port connector 260 fluidly connects the treatment port 240B with the inner lumen of the distal valve 200B to provides a means for conveying a treatment medium into and/or out from the inner lumen.

As shown, the fill port connector 250 of the distal valve 200B includes the rear fitting 224B attached to the rear ring 218B, where the fill port 210B is located. The fill port connector 250 also includes the outer tube 204B connected to the front ring 220B. The treatment port connector 260 includes a rear ring 218C which connects to the front ring 220B of the fill port connector 250. The treatment port connector 260 also includes an outer tube 204C as well as a front ring 220C which connects to the front fitting 226B, where the treatment port 240B is located. The connections may be achieved via complementary threads, adhesives, snap fits, fasteners and/or other mechanisms, for example.

The fill port connector 250 and the treatment port connector 260 may be formed separately and then connected or conjoined together to form the distal valve 200B. Additionally, other connectors may be attached between the fill port connector 250 and the treatment port connector 260, or more specifically, between the front ring 220B of the fill port connector 250 and the rear ring 218C of the treatment port connector 260. In some examples, an additional port connector 270, as shown in FIG. 2B, with an additional port 210D, a rear ring 218D, front ring 220D, an outer tube 204D, and a coupling feature 211D associated with the rear ring 218D may be implemented to introduce additional fluid into the treatment system 100. In such embodiments, the rear ring 218D connects to the front ring 220B, and the front ring 220D connects to the rear ring 218C. Any number of such additional port connectors 270 may be implemented in the distal valve 200B, as suitable.

Inclusion of one or more of the additional port connectors allows for different treatment media to be introduced at different times for more flexible treatment. For example, if a second treatment medium is to be introduced at a certain time after the first treatment medium, the first treatment medium may be introduced via a first treatment port (e.g., 210B) and when the time comes to introduce the second treatment medium, a second treatment port (e.g., 210D) may be used to do so. The two treatment mediums may be any of the prior examples, such as saline, carbon dioxide, perfluorocarbon solution, methylene blue, or others. Each coupling feature may be attached to a syringe or other delivery device containing a different treatment medium. In some examples, by having more than one treatment port may help obviate the need to switch between different delivery devices when changing from one treatment medium to another.

The treatment system 100 may be utilized with a variety of types of endoluminal devices, including the examples shown in FIGS. 6 to 9, which are all generically referred to by reference number 600 (apart from dilator 500 shown in FIG. 1B, which is also an endoluminal device).

Figures 6, 7A, 7B:
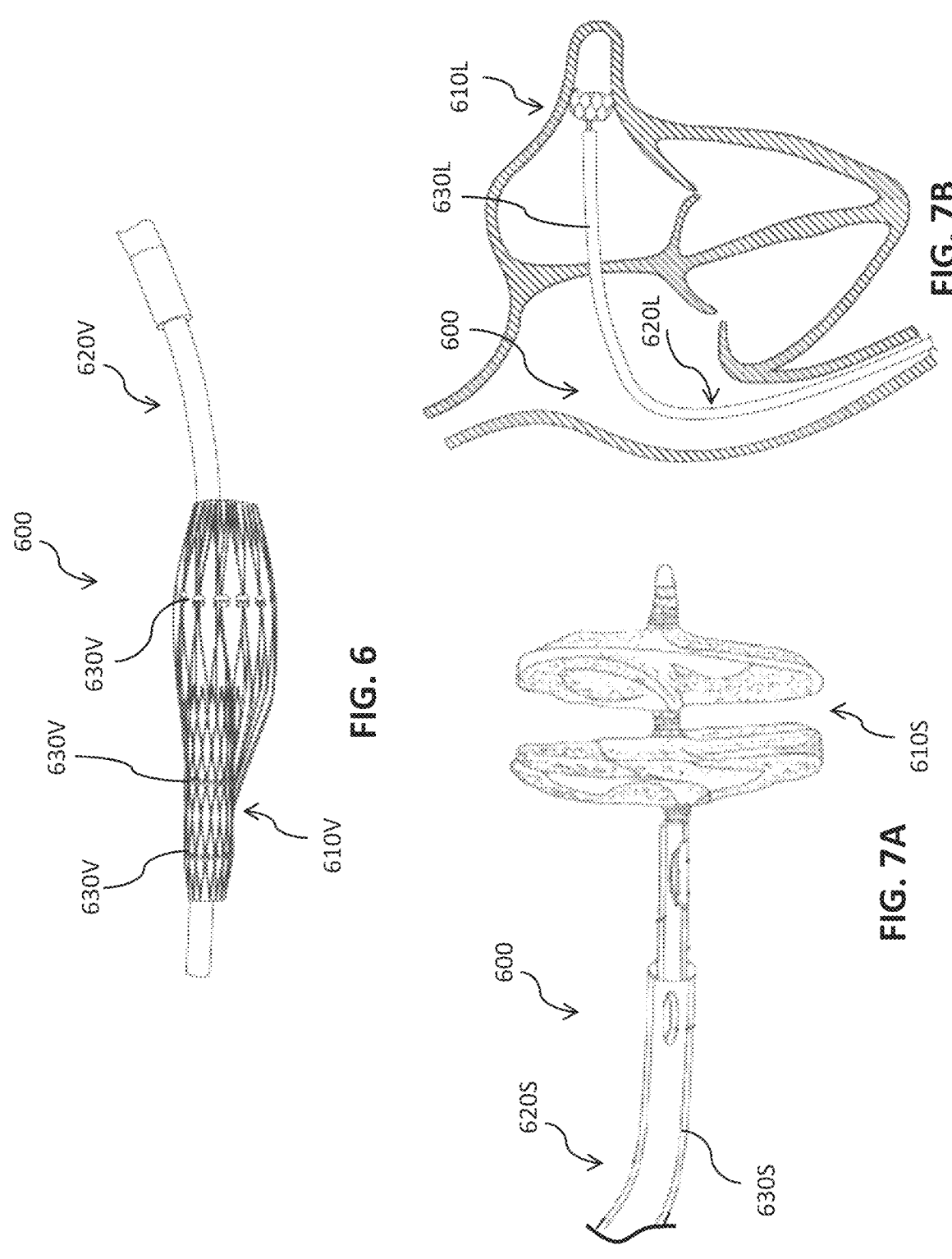
FIG. 6 shows an endoluminal device to be used in association with a delivery system, the endoluminal device being in the form of an implantable prosthetic valve maintained on a delivery catheter, according to some embodiments.
FIGS. 7A and 7B shows endoluminal devices to be used in association with a delivery system, the endoluminal device being in the form of implantable occluders maintained on a delivery catheter, according to some embodiments.

FIG. 6 shows an endoluminal device 600 in the form of a transcatheter delivery system including a catheter and an implantable device maintained at a compacted, delivery diameter or state by the delivery catheter. The implantable device defines a treatment portion, or a part of the endoluminal device 600 for which a treatment is to be performed upon. In particular, the endoluminal device 600 in FIG. 6 includes a prosthetic valve 610V (e.g., a prosthetic heart valve) maintained in a diametrically compacted state by a delivery catheter 620V. As shown, the delivery catheter 620V employs a fiber constraining delivery system, such as that described in U.S. application Ser. No. 16/129,657, entitled "Transcatheter Deployment Systems and Associated Methods," filed Sep. 12, 2018. The prosthetic valve 610V can be transferred between a fully compacted, delivery diameter or state, a partially compacted treatment diameter (e.g., as shown in FIG. 6), and a fully expanded, deployed diameter using the delivery catheter 620V, which tightens and loosens constraints 630V releasably coupled to the prosthetic valve 610V.

FIG. 7A shows an endoluminal device 600 in the form of a transcatheter delivery system including a catheter and an implantable device maintained at a compacted, delivery diameter or state by the delivery catheter. The implantable device is included in the treatment portion, or part of the endoluminal device 600 for which a treatment is to be performed upon. In particular, the endoluminal device 600 in FIG. 7A includes a septal occluder 610S (e.g., atrial septal occluder) maintained in a diametrically compacted state by a delivery catheter 620S. As shown, the delivery catheter 620S employs a sheath, or tube constraining delivery system, such as that described in U.S. Pat. No. 8,956,389, entitled "Sealing Device and Delivery System." The septal occluder 610S can be transferred between a fully compacted, delivery diameter or state, a partially compacted treatment diameter, and a fully expanded, deployed diameter (e.g., as shown in FIG. 7A) using the delivery catheter 620S, which extends and retracts the septal occluder 610S from sheath, or tube 630S associated with the delivery catheter 620S.

FIG. 7B shows an endoluminal device 600 in the form of a transcatheter delivery system including a catheter and an implantable device maintained at a compacted, delivery diameter or state by the delivery catheter. The implantable device is included in the treatment portion, or part of the endoluminal device 600 for which a treatment is to be performed upon. In particular, the endoluminal device 600 in FIG. 7B includes an occluder 610L (e.g., left atrial appendage occluder) maintained by a delivery catheter 620L. As shown, the delivery catheter 620L employs a sheath, or tube constraining delivery system, such as that described in PCT Application Publication WO 2016/183495, entitled "Devices and Methods for Occlusion of an Atrial Appendage." The occluder 610L can be transferred between a fully compacted, delivery diameter or state, a partially compacted treatment diameter, and a fully expanded, deployed diameter (e.g., as shown in FIG. 7B) using the delivery catheter 620L, which extends and retracts the occluder 610L from sheath, or tube 630L associated with the delivery catheter 620L.

Figures 8, 9:
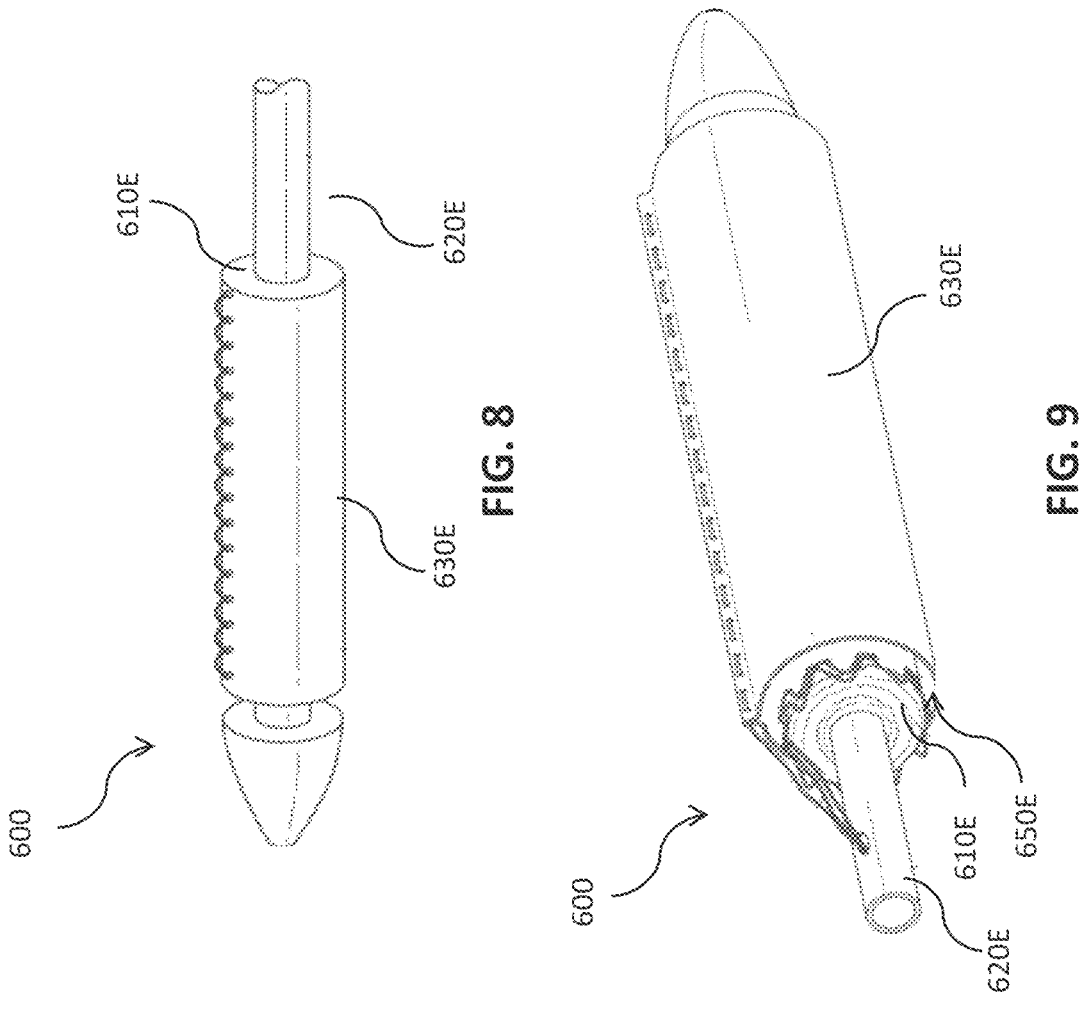
FIG. 8 shows an endoluminal device to be used in association with a delivery system, the endoluminal device being in the form of an implantable endoprosthesis maintained on a delivery catheter in a compacted stated by a retention sleeve, according to some embodiments.
FIG. 9 is an isometric view of the endoprosthesis of FIG. 8 with additional retention sleeve and endoprosthesis details shown by way of example, according to some embodiments.

FIGS. 8 and 9 shows an endoluminal device 600 in the form of a transcatheter delivery system including a catheter and an implantable device maintained at a compacted, delivery diameter or state by the delivery catheter. The implantable device defines a treatment portion, or a part of the endoluminal device 600 for which a treatment is to be performed upon. In particular, the endoluminal device 600 in FIGS. 8 and 9 includes an endoprosthesis 610E (e.g., stent graft) maintained in a diametrically compacted state by a delivery catheter 620E. As shown, the delivery catheter 620E employs a retention sleeve constraining delivery system, such as that described in U.S. Pat. No. 9,592,143, entitled "Sleeves for Expandable Medical Devices." The endoprosthesis 610E can be transferred between a fully compacted, delivery diameter or state (e.g., as shown in FIGS. 8 and 9) and a fully expanded, deployed diameter using the delivery catheter 620E, which releases the retention sleeve 630E to deploy the endoprosthesis 610E carried by the delivery catheter 620E.

As described in further detail, some methods of treating an endoluminal device for introduction into a body of a patient include positioning the endoluminal device into the treatment system 100; closing the proximal valve 200A and the distal valve 200B to seal the proximal valve 200A against the first portion of the endoluminal device and the distal valve 200B against the second portion of the endoluminal device; and delivering a treatment medium into the treatment space to expose a portion of the endoluminal device to be treated, or the treatment portion of the endoluminal device, to the treatment medium.

In some examples, the treatment portion of the endoluminal device includes an implantable device maintained by a delivery catheter. The treatment portion of the endoluminal device may include a proximal portion of an implantable device with a distal portion of the endoluminal device extending from the distal valve. In various examples, delivering a treatment medium into the treatment space forces air from the treatment portion of the endoluminal device. In particular, delivering the treatment medium into the treatment space through at least one of a proximal treatment portion in fluid communication with a proximal portion of the treatment chamber, and a distal treatment portion in fluid communication with a distal portion of the treatment chamber, forces entrapped air from a portion of the endoluminal device (e.g., an implantable device).

In some examples, the treatment medium exits the treatment chamber 300 through the treatment port 230B which is in fluid communication with a distal portion of the treatment chamber 300. The endoluminal device may include a retention sleeve that maintains an implantable device in a compacted, delivery state, and the distal valve may be closed over the sleeve such that the treatment medium exits the treatment chamber 300 from the distal valve 200B through one or more gaps between the sleeve and the implantable device. Some methods also include inserting the introducer sheath into a body lumen of the patient, either before, during, or after endoluminal device treatment.

Figure 10:
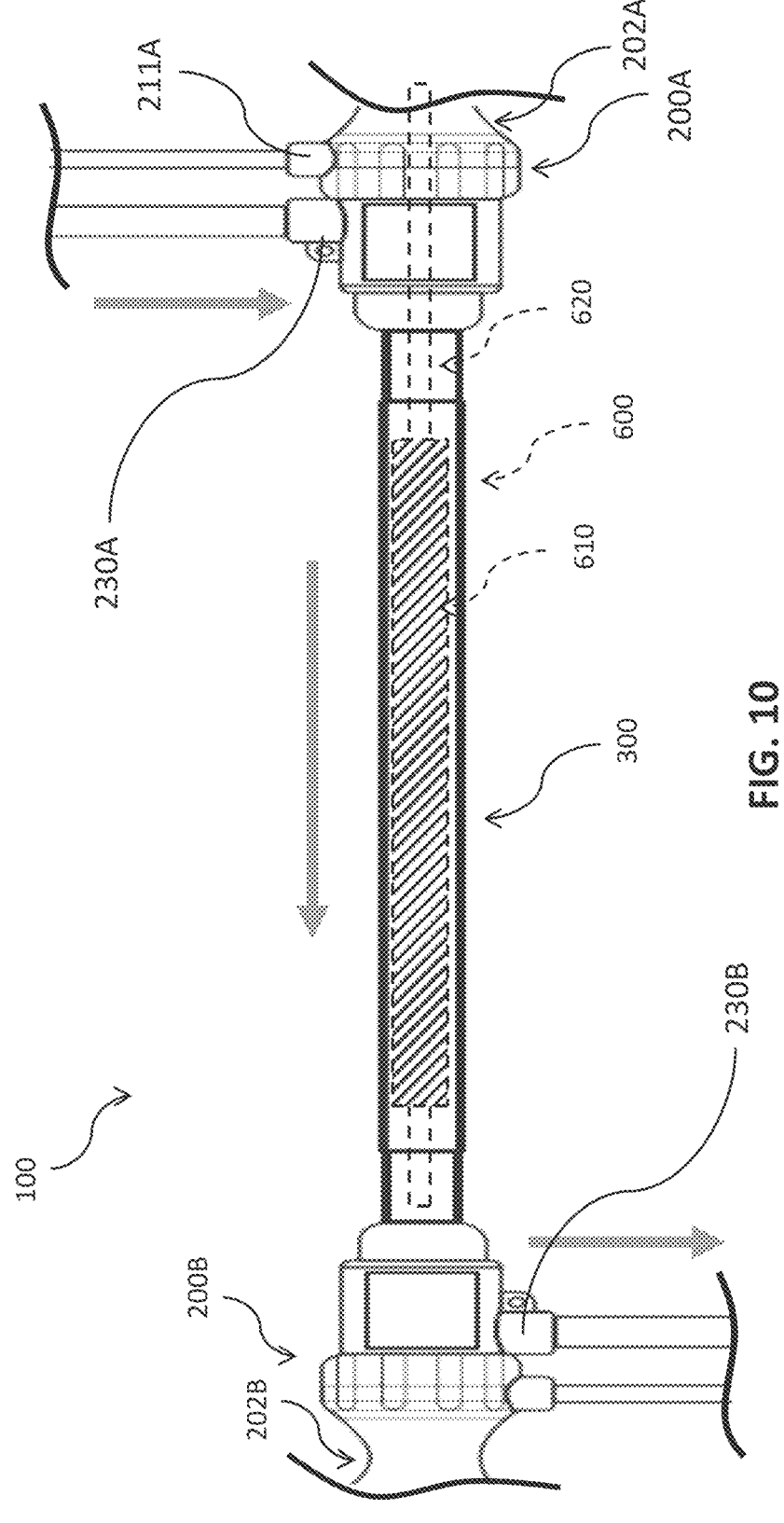
FIG. 10 is a close-up, partial view of a portion of the treatment system of FIG. 1A and an associated endoluminal device received by the treatment system according to one method of treating the endoluminal device, according to some embodiments.

FIG. 10 is a close-up, partial view of a portion of the treatment system of FIG. 1A and an associated endoluminal device received by the treatment system according to a method of treating the endoluminal device, according to some embodiments. An endoluminal device 600 including an implantable device 610 carried by a delivery catheter 620 is represented generally by broken line boxes to show relative component positions in a schematic fashion. In other words, the relative positions of the generalized components of the endoluminal device 600 are superimposed over the treatment system 100 for visualization purposes. In some examples, the delivery catheter 620 has a longitudinally collapsible configuration. For example, a portion of the delivery catheter 620 may include a plurality of creases, folds, or pleats similar to the bellows of an accordion, such that when a longitudinal force is applied, the pleats collapse to shorten the length of the delivery catheter 620. In some examples, the delivery catheter 620 may be separable by breaking or splitting. In some examples, a row of apertures or perforations may be formed along at least a portion of a length of the delivery catheter 620 such that, when enough radial force is applied to the delivery catheter 620, the surface of the delivery catheter 620 may be torn, causing the delivery catheter 620 to break away from the endoluminal device 600.

In some examples, the distal sheath 400 is inserted into a body of a patient, e.g., into the vasculature of the patient with the assistance of the dilator 500. The dilator 500 is removed from the treatment system 100 and the endoluminal device 600 is translated into the treatment system 100 with the implantable device 610 positioned in the treatment chamber 300 between the proximal seal mechanism 202A and the distal seal mechanism 202B with the proximal valve 200A pressurized and closed to form a seal around the endoluminal device 600 and the distal seal mechanism pressurized and closed to form a seal. In this manner, the implantable device 610 (e.g., a stent graft or prosthetic valve) is located in the sealed treatment space between the proximal valve 200A and the distal valve 200B. In examples where portions of the treatment system 100 are transparent (e.g., portions of the proximal valve 200A and the distal valve 200B, and/or treatment chamber 300), a user may visually confirm proper positioning. It should be noted that the distal sheath 400 is located in the body of the patient prior to device treatment in some embodiments only, and in others the treatment occurs prior to insertion of the treatment system 100.

Regardless, with both the proximal valve 200A in a closed, or sealed state around the endoluminal device 600, and in particular the delivery catheter 620, and the distal valve 200B in a closed, or sealed state, a treatment medium is delivered into the treatment space of the treatment chamber 300 using the treatment ports 230A, 230B. For example, pressure sources (e.g., a pressure reservoir such as a syringe or pressurized gas source) are attached to each of the treatment ports 230A, 230B and a treatment medium (e.g., saline, carbon dioxide, perfluorocarbon solution, methylene blue, or others) is delivered into the treatment chamber 300. The treatment medium may be "pushed" into treatment chamber 300 through positive pressure through the treatment port 230A and "drawn" into to treatment chamber 300 through negative pressure through the treatment port 230B and vice versa. Or, alternatively, positive pressure or negative pressure alone is applied through one of the treatment ports 230A, 230B to introduce the treatment medium into the treatment chamber 300.

The implantable device 610 may be treated in a partially or fully expanded state if the treatment chamber 300 is sized appropriately (e.g., of sufficient diameter) and if a user so desires. It may be advantageous to treat the implantable device 610 in a partially or fully expanded state (assuming the delivery catheter 620 and associated retention mechanism is capable of reversing expansion or reverse expansion is not required) as more device surface area is accessible during device treatment, which may speed up and enhance treatment efficacy.

In some examples, once the implantable device 610 has been treated as desired (e.g., flushed of air, wetted out, or otherwise treated), the treatment port 240B (FIG. 1A) may be opened and blood may be pulled into the distal sheath 400 (e.g., by attaching a syringe and applying a negative pressure through the treatment port 240B). Once the distal sheath 400 is full of blood, the distal valve 200B may be opened, or released, to fill the treatment chamber 300 and associated treatment space with blood. The implantable device 610 may then be tracked to a desired location within the body by advancing the implantable device 610 through and out from the distal sheath 400 of the treatment system 100 (e.g., by tracking the implantable device 610 over a guidewire).

Figures 11A, 11B, 11C:
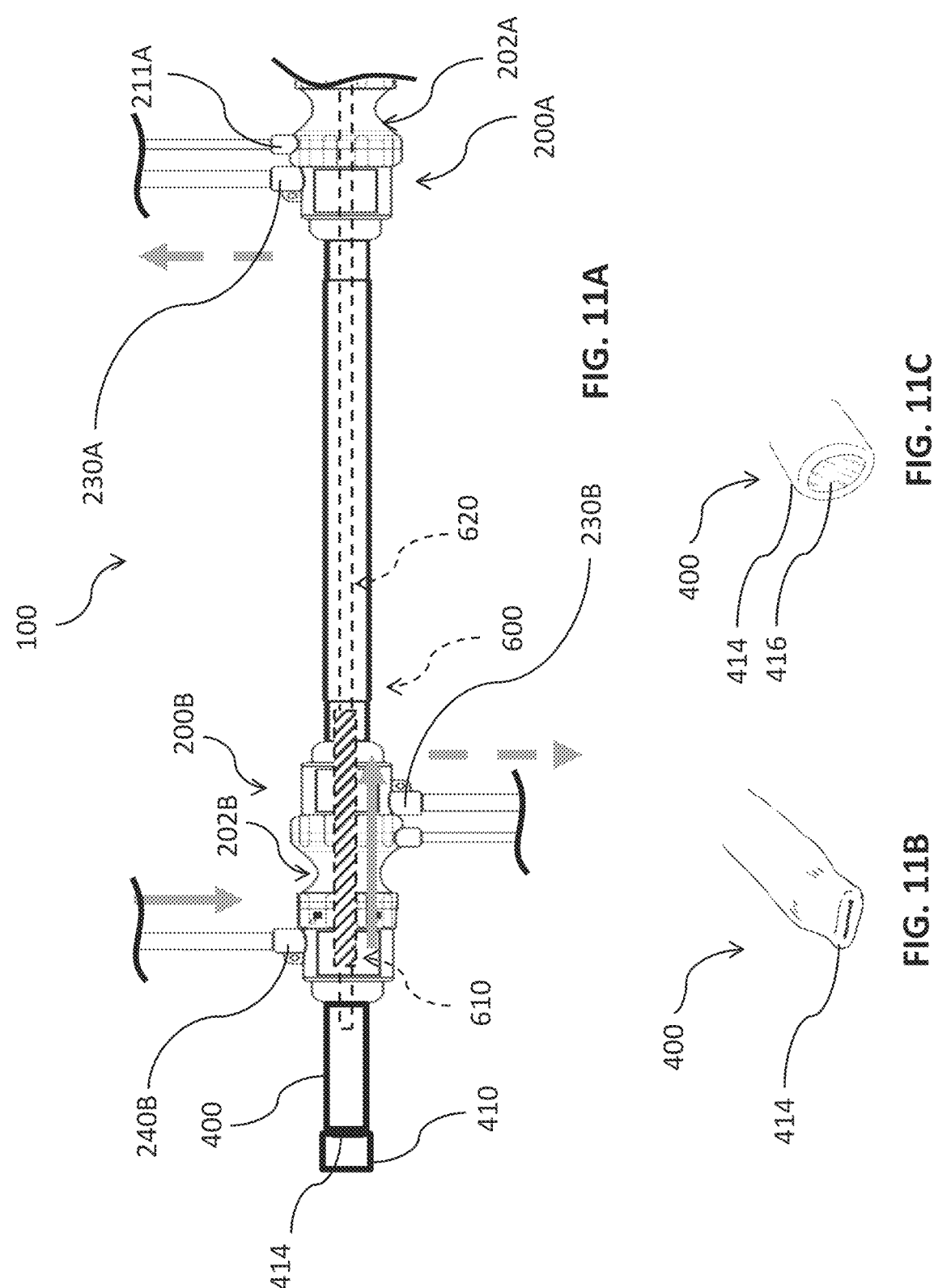
FIG. 11A is a close-up, partial view of a portion of the treatment system of FIG. 1A and an associated endoluminal device received by the treatment system according to another method of treating the endoluminal device, according to some embodiments.
FIG. 11B is a close-up, partial view of a portion of a tube as implemented in the treatment system of FIG. 1A according to some embodiments.
FIG. 11C is a close-up view of a cap member as implemented in the delivery system of FIG. 11A according to some embodiments.

FIG. 11A is a close-up, partial view of a portion of the treatment system of FIG. 1A with the endoluminal device 600 in an adjusted treatment position relative to that shown in FIG. 10, according to other methods of treating the endoluminal device 600.

In the example of FIG. 11A, treatment would more typically occur prior to inserting the distal sheath 400 into a body of a patient. In some examples, a distal end of the distal sheath 400 may be truncated (e.g., precut) or may be full length. As shown in FIG. 11A, the distal sheath 400 is shortened, or truncated though such truncation is not required. Additionally, the distal end of the distal sheath 400 is capped or otherwise sealed with a cap member 410 illustrated generally in FIG. 11A. The cap member 410 may be a threaded, dead head cap, a plug, or other implement, or the end may be sealed manually with a user's thumb acting as the cap member 410.

In some examples, the cap member 410 may be replaced with a clamp, plug, or other sealing member. For example, a hose clamp or any other suitable vascular clamp (e.g., a "Cooley" clamp) may be employed to pinch the distal end of the distal sheath 400 (e.g., distal sheath 400 is formed of flexible tubing material). Regardless, the seal at the distal end may be temporary or permanent, as appropriate. In some examples, a distal end 414 of the tube 412 may be bonded together (e.g., being at least partially flattened to form a "duck bill" configuration as shown in FIG. 11B and sealed closed). In some examples, the distal end of the tube may be heated and/or subsequently closed, crushed, or sealed together in any suitable configuration to form a seal in a distal end of the tube.

In the example of FIG. 11C, the cap member 410 includes a breakable seal 416 at a distal end of the cap member 410. The breakable seal 416 is broken, torn, or punctured manually by pushing the endoluminal device 600 or other instrument against the breakable seal 416. The breakable seal 416 may be a membrane or a film (e.g., a self-healing membrane) made of a polymer material. Inclusion of a seal may help ensure that, following treatment in the treatment chamber, the implantable device 610 does not come into contact with the environment (e.g., ambient air) after being treated. In particular, prior to breaking the breakable seal 416, the distal sheath 400 may be coupled to an introducer sheath, valve, or other device for directly insertion into the patient.

As shown, the endoluminal device 600 is translated into the treatment chamber 300 with the implantable device 610 located in the distal valve 200B, with either end, or end portion, of the implantable device 610 on either end of distal seal mechanism 202B. In examples where portions of the treatment system 100 are transparent (e.g., portions of the proximal valve 200A and the distal valve 200B, and/or treatment chamber 300), a user may visually confirm proper positioning of the implantable device 610.

In the example of FIG. 11A, the treatment space is extended into the distal sheath 400 to include the capped, distal sheath 400. Thus, the distal sheath 400 can be said to be acting as an alternative or additional treatment chamber. With the each of the proximal valve 200A and the distal valve 200B pressurized and closed to form a seal around the endoluminal device 600, a treatment medium is delivered into the treatment space of the distal sheath 400 using the treatment port 240B, as shown by the solid arrow. For example, pressure sources (e.g., a pressure reservoir, such as a pressurized gas source or a syringe) is attached to the treatment port 240B and a treatment medium (e.g., carbon dioxide, saline, perfluorocarbon solution, methylene blue, or others) is delivered into the distal sheath 400. When sufficient back pressure is applied, the pressurized treatment medium forces its way through any folds, creases, or gaps present in the implantable device 610 or that are present between the implantable device and any associated retention mechanism (e.g., not shown, but such as a retention sleeve). The pressurized treatment medium then passes "through" the gaps past the closed distal valve 200B, into the treatment chamber 300, and out from one or both treatment ports 230A, 230B as desired, as shown by the broken arrows.

Such a process can be particularly advantageous for forcing any entrapped air from folds, creases, or gaps in the implantable device 610 and/or that exist between the implantable device 610 and any associated retention mechanism (e.g., not shown, but such as a retention sleeve). It can be particularly helpful that the distal valve 200B is closed around the outer perimeter of the implantable device 610 and any associated retention mechanism (not shown), as the treatment medium is less apt to simply pass around the implantable device 610 and retention mechanism, but is instead forced to pass through the gaps, folds, creases and spaces in which air may be entrapped.

It should be understood that the reverse flow of treatment medium may also be effectively applied in the context of FIG. 11A. Restated, the positive pressure may be applied through one or both of the treatment ports 230A, 230B, with the treatment medium forced from the treatment chamber 300, through the implantable device 610 across the closed distal valve 200B, into the capped distal sheath 400, and out from the treatment port 240B (alternatively, the cap member 410 may be omitted and the treatment medium may simply pass from the end of the distal sheath 400 as desired. In the examples described in association with FIG. 11A, the implantable device 610 is generally treated in a fully compacted state, as the distal valve 200B is sealed over the implantable device 610, though not necessarily in all instances.

In various examples, once the implantable device 610 has been treated as desired (e.g., flushed of air, wetted out, or otherwise treated), the treatment system 100 may be introduced into the body of a patient and delivery of the implantable device 610 may proceed in a similar manner to that previously described.

Figures 12A, 12B:
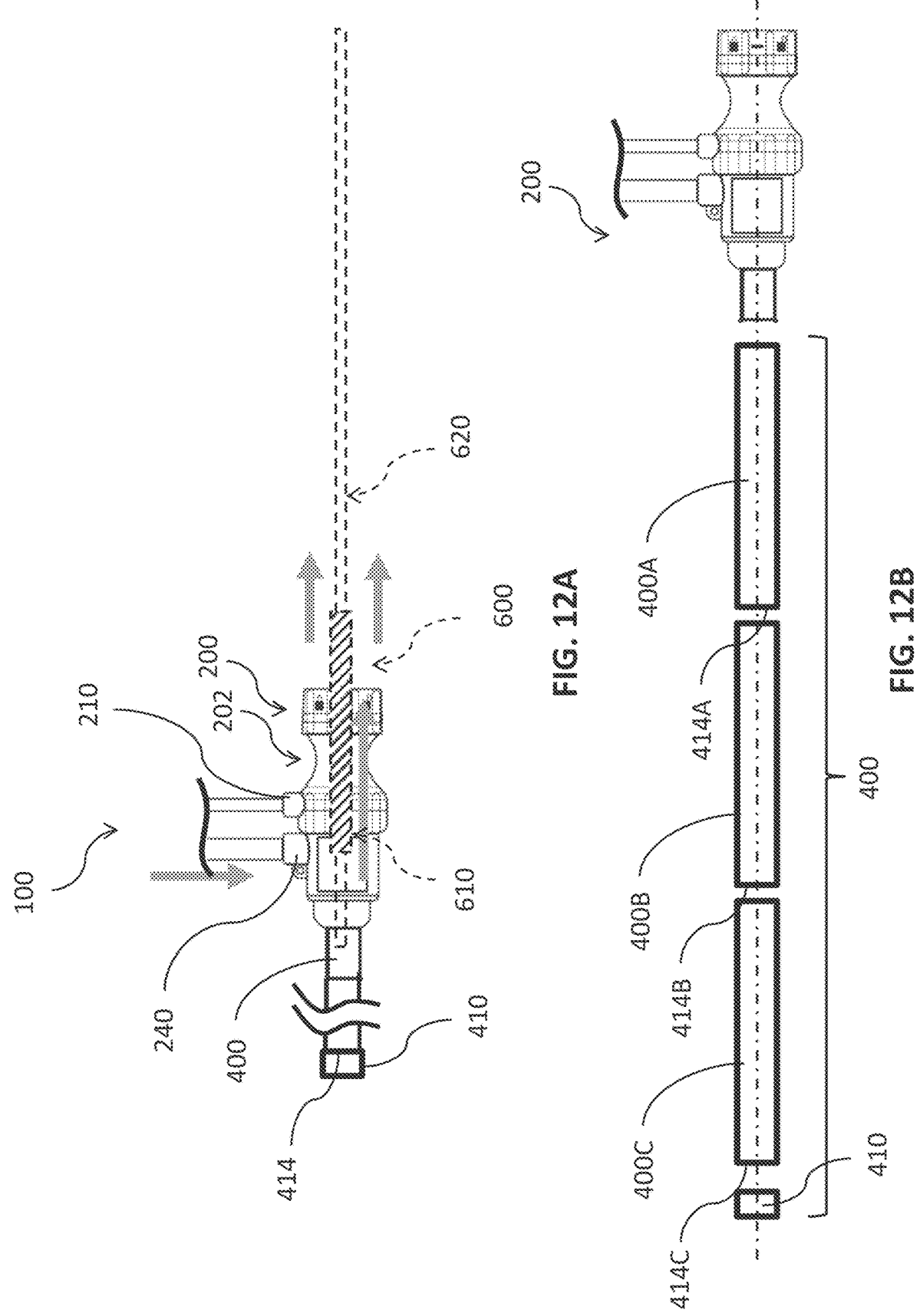
FIG. 12A is a close-up, partial view of a portion of another treatment system and an associated endoluminal device received by the treatment system according to a method of treating the endoluminal device, according to some embodiments.
FIGS. 12B to 12G are close-up, partial views of portions of other treatment systems, according to some embodiments.

FIG. 12A is a close-up, partial view of a portion of another treatment system 100, which may be a delivery system, and an associated endoluminal device 600 received by the treatment system 100 according to a method of treating the endoluminal device 600, according to some embodiments. As shown in FIG. 12A, the proximal valve 200A is omitted from the treatment system 100 in favor of a single valve 200 that is substantially similar to the proximal valve 200A and the distal valve 200B. Thus, the valve 200 includes generally the same features as those of the proximal valve 200A and/or the distal valve 200B and the features of the valve 200 are referred to by the same reference numbers as those of the proximal valve 200A and the distal valve 200B, except those reference numbers are not followed by an "A" or a "B."

Though a single valve is employed, the methodology may be similar to that described above with reference to FIG. 11A, according to various examples. As shown in FIG. 12A, the distal sheath 400 serves as a treatment chamber, and may alternatively be referred to as a treatment chamber.

In the example of FIG. 12A, treatment would more typically occur prior to inserting the distal sheath 400 into a body of a patient, but not in all cases. In some examples, a distal end of the distal sheath 400 may be truncated (e.g., precut) or may be full length. As shown in FIG. 12A, the distal sheath 400 is shortened, or truncated. Additionally, the distal end of the distal sheath 400 is capped or otherwise sealed with a cap member 410 illustrated generally in FIG. 12A. The cap member 410 may be a threaded, dead head cap, a plug, or other implement, such as a user's thumb and is represented generally in FIG. 12A. In each of the instances previously described, when a finger or thumb of a user is utilized to seal the distal sheath 400 (also described as a treatment chamber), it may be referred to as digitally sealing the distal sheath 400 (or treatment chamber). In some examples, the cap member 410 may be replaced with a clamp, plug, or other sealing member. For example, a hose clamp or any other suitable vascular clamp (e.g., a "Cooley" clamp) may be employed to pinch the distal end of the distal sheath 400 (e.g., distal sheath 400 is formed of flexible tubing material). Regardless, the seal at the distal end may be temporary or permanent, as appropriate. In some examples, a distal end 414 of the tube 412 may be bonded together (e.g., being at least partially flattened to form a "duck bill" configuration as shown in FIG. 11B and sealed closed). In some examples, the distal end of the tube may be heated and/or subsequently closed, crushed, or sealed together in any suitable configuration to form a seal in a distal end of the tube.

As shown, the endoluminal device 600 is translated into the seal mechanism 202 of the valve 200, with either end of the implantable device 610 on either end of the seal mechanism 202. In examples where portions of the treatment system 100 are transparent (e.g., portions of the valve 200, such as the front fitting 226), a user may visually confirm proper positioning of the implantable device 610.

As shown, the distal portion of the implantable device 610 is positioned in the treatment space defined by the distal sheath 400. Thus, in the example of FIG. 12A, the treatment space is extended to include the capped, distal sheath 400. With the valve 200 pressurized and closed to form a seal around the endoluminal device 600, a treatment medium is delivered into the treatment space as defined by the distal sheath 400, which is acting as a treatment chamber, using the treatment port 240. For example, pressure sources (e.g., a pressure reservoir, such as a pressurized gas source or a syringe) is attached to the treatment port 240 and a treatment medium (e.g., carbon dioxide, saline, perfluorocarbon solution, methylene blue, or others) is delivered into the distal sheath 400, acting as the treatment chamber. When sufficient back pressure is applied, the pressurized treatment medium forces its way through any folds, creases, or gaps present in the implantable device 610 or that are present between the implantable device and any associated retention mechanism (e.g., not shown, but such as a retention sleeve). The pressurized treatment medium then passes "through" the gaps past the closed valve 200 and out from the other end of the implantable device 610 and/or associated retention mechanism (e.g., not shown, but such as a retention sleeve positioned around the implantable device 610). The direction of the flow of the pressured treatment medium is shown by the arrows in FIG. 12A.

It can be particularly helpful that the valve 200 is closed around the outer perimeter of the implantable device 610 and any associated retention mechanism, as the treatment medium is less apt to simply pass around the implantable device 610 and any retention mechanism, but is instead forced to pass through the gaps, folds, creases and spaces in which air may be entrapped.

In various examples, once the implantable device 610 has been treated as desired (e.g., flushed of air, wetted out, or otherwise treated), the treatment system 100 may be introduced into the body of a patient and delivery of the implantable device 610 may proceed in a similar manner to that previously described.

FIG. 12B shows additional or alternative features of the treatment system 100 according to FIG. 12A, and in particular a potential modification of the distal sheath 400, according to various examples. As shown in FIG. 12B, the distal sheath 400 serves as a treatment chamber, and may alternatively be referred to as a treatment chamber. As shown, the distal sheath 400 may include a plurality of sections, such as a first section 400A, a second section 400B, and a third section 400C. Each section of the distal sheath 400 may be configured to be removably coupled to another section and/or the valve 200. In this manner, a user of the treatment system 100 may use one or more of the first section 400A, the second section 400B, and the third section 400C as desired to select a length of the distal sheath 400. Coupling mechanisms such as male and female threaded ends may be employed between the sections, such as at the distal end 414A of the first section 400A and/or the distal end 414B of the second section 414B. Although three sections are shown, fewer (e.g., two) or greater (e.g., more than 3, 4 or more, or any number as desired) may be implemented to achieve the desired degree of adjustability.

Figures 12C, 12D:
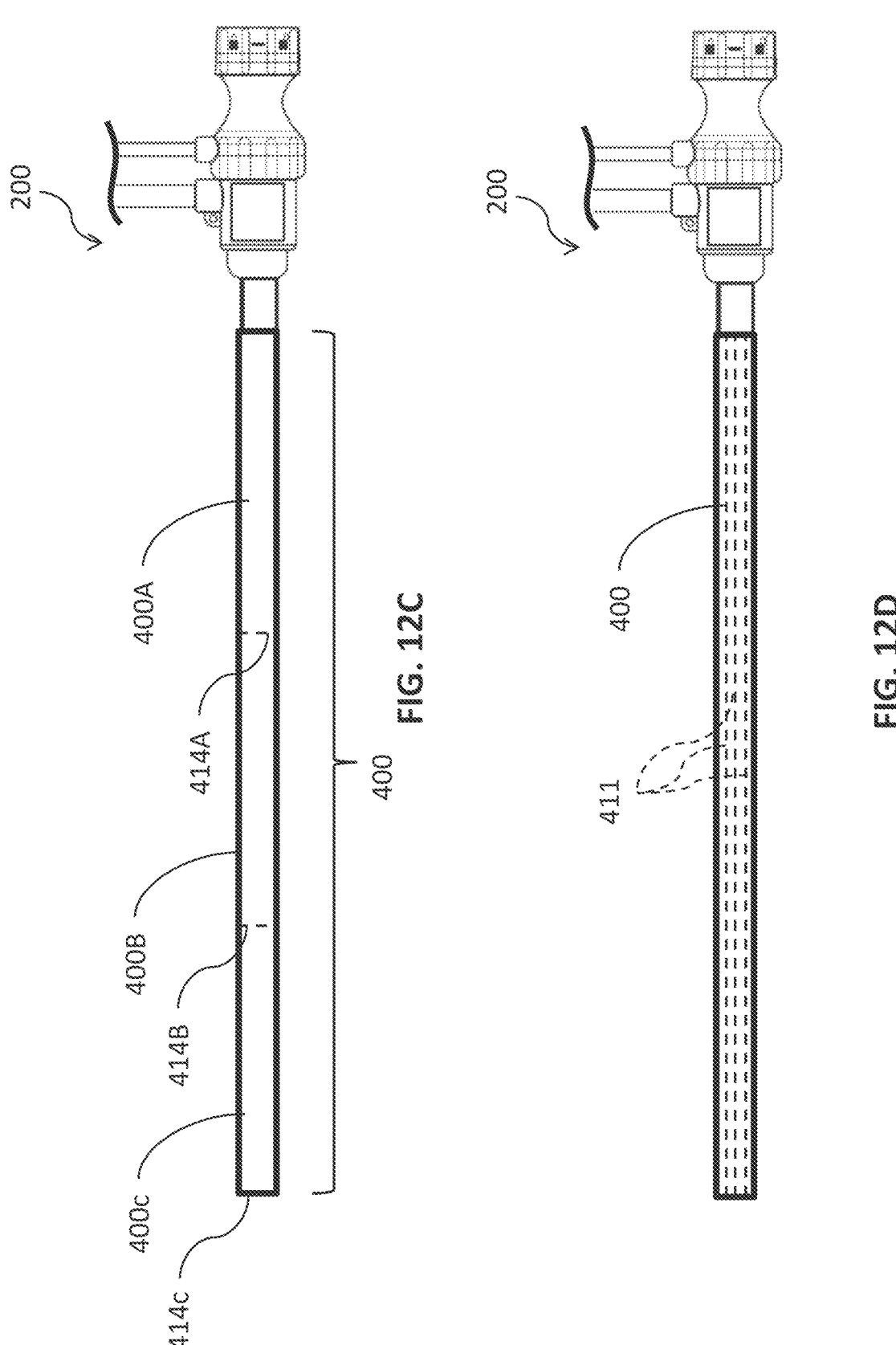

As a further feature, as shown in FIG. 12C the sections may have a "break away" coupling between them (e.g., scribed lines or weakened areas between the sections such that one or more of the sections is configured to be manually removed. Alternatively, the sections may simply be cut using scissors or knife and then capped or clamped as appropriate. FIG. 12C shows additional or alternative features of the treatment system 100 according to FIG. 12A, and in particular a potential modification of the distal sheath 400, according to various examples. As shown in FIG. 12C, the distal sheath 400 serves as a treatment chamber, and may alternatively be referred to as a treatment chamber. As shown, the distal sheath 400 may include a plurality of sections, such as a first section 400A, a second section 400B, and a third section 400C. Each section of the distal sheath 400 may be configured to be removably coupled to another section and/or the valve 200 at a frangible connection (e.g., a scored or other weakened portion) at which the respective first section 400A, second section 400B, and third section 400C may be separated. In this manner, a user of the treatment system 100 may remove one or more of the third section 400C and the second section 400B as desired to select a length of the distal sheath 400. Although three sections are shown, fewer (e.g., two) or greater (e.g., more than 3, 4 or more, or any number as desired) may be implemented to achieve the desired degree of adjustability.

As a further feature, as shown in FIG. 12D the distal sheath 400 may include one or more longitudinally splittable features 411 in the form of longitudinal score lines, frangible sections or weakened areas to permit tearing away, cutting, separating or otherwise removing the distal sheath (e.g., from around the endoluminal device 600 (not shown). In use, an operator (not shown) may cut, tear, or otherwise split the distal sheath 400 along the longitudinally splittable features 411 to separate, and optionally remove, the distal sheath 400. Though relatively straight longitudinally splittable features are shown, helically oriented features are also contemplated.

Figure 12E:
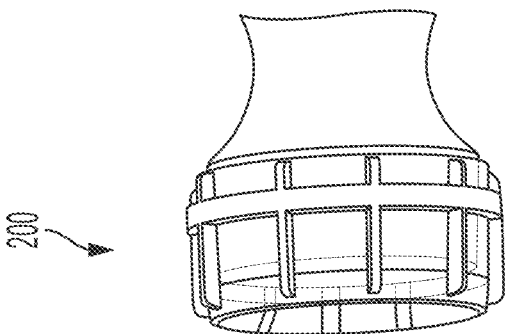
Figure 12E:
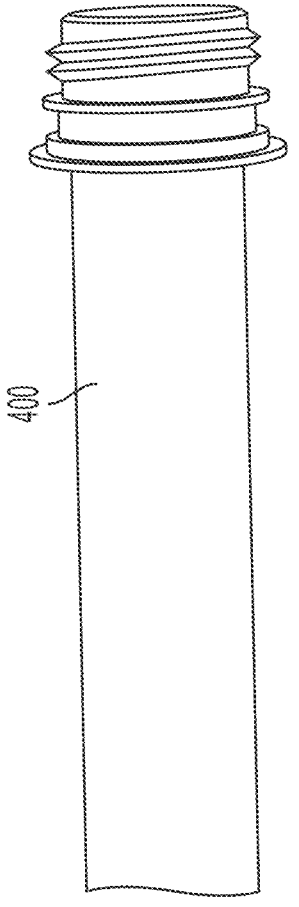

As a further feature, as shown in FIG. 12E the distal sheath 400 may have threading or other removably coupling features and may be provided as a kit of parts along with a variety of distal sheaths (not shown) of different lengths. In such an instance, a user (not shown) may simply select the distal sheath 400 of the desired length and removably attach the distal sheath 400 to the valve 200.

Figures 12F, 12G:
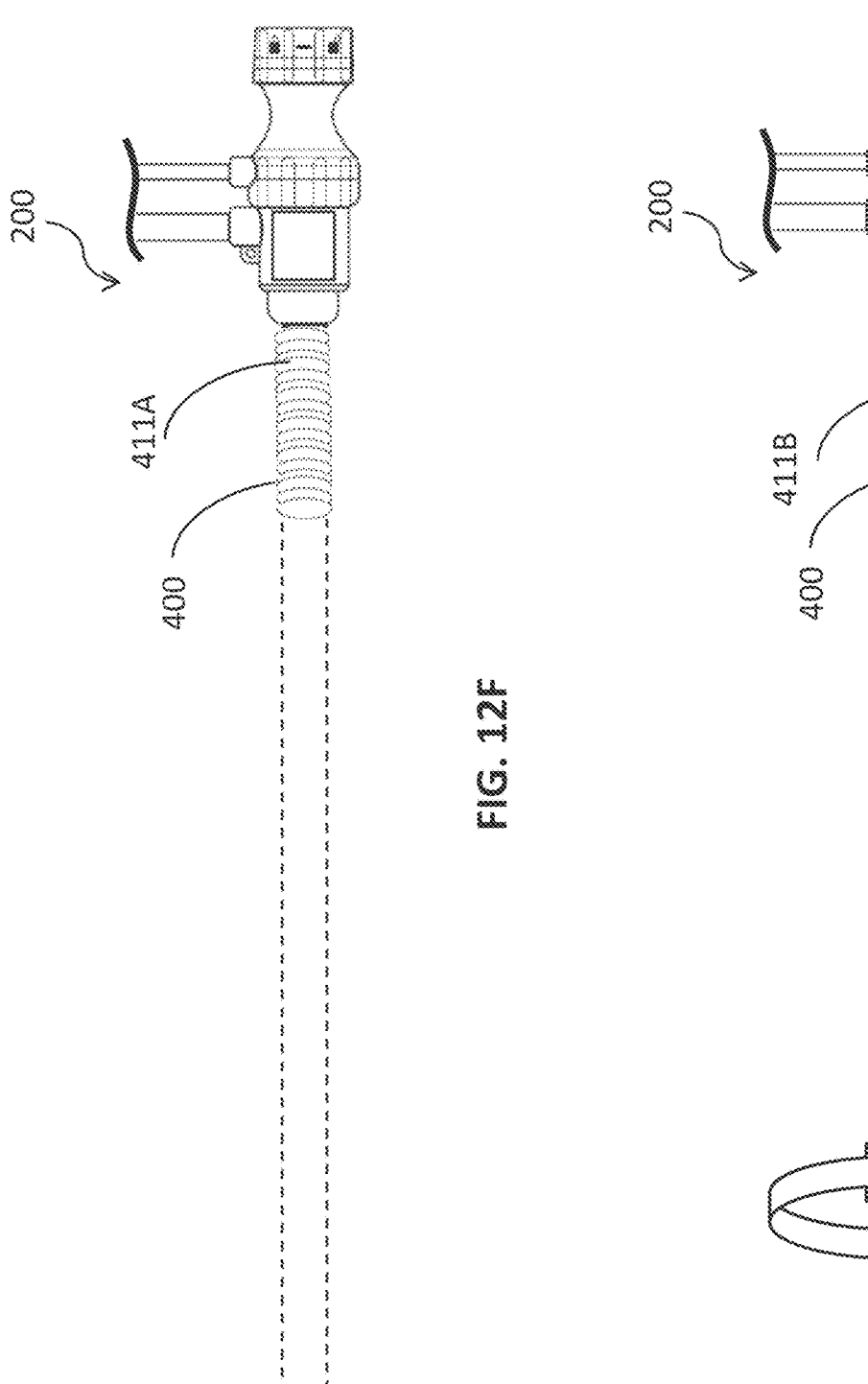

As a further feature, as shown in FIG. 12F the distal sheath 400 may be longitudinally collapsible (e.g., in the manner of an accordion) to reduce or extend the length of the distal sheath 400. For reference, FIG. 12F shows the distal sheath 400 in an extended state in broken lines and in a longitudinally collapsed state in solid lines with accordion wrinkles, or folds 411a. In some examples, the distal sheath 400 is adjustable in length through any of a variety of desired lengths by longitudinally corn pressing or extending the distal sheath 400.

As a further feature, as shown in FIG. 12G the distal sheath 400 may be longitudinally collapsible (e.g., in the manner of a helically wound member) by twisting the distal sheath 400 to cause a reduction in overall length. In some examples, the distal sheath 400 includes a helical wrap, or layered assembly that while sealed, may be twisted to cause relative movement of the helical wrap or layers 411B to reduce or extend the length of the distal sheath 400. In some examples, the distal sheath 400 is adjustable in length through any of a variety of desired lengths by longitudinally compressing or extending the distal sheath 400 by twisting the distal sheath 400 in an appropriate direction.

Figure 13:
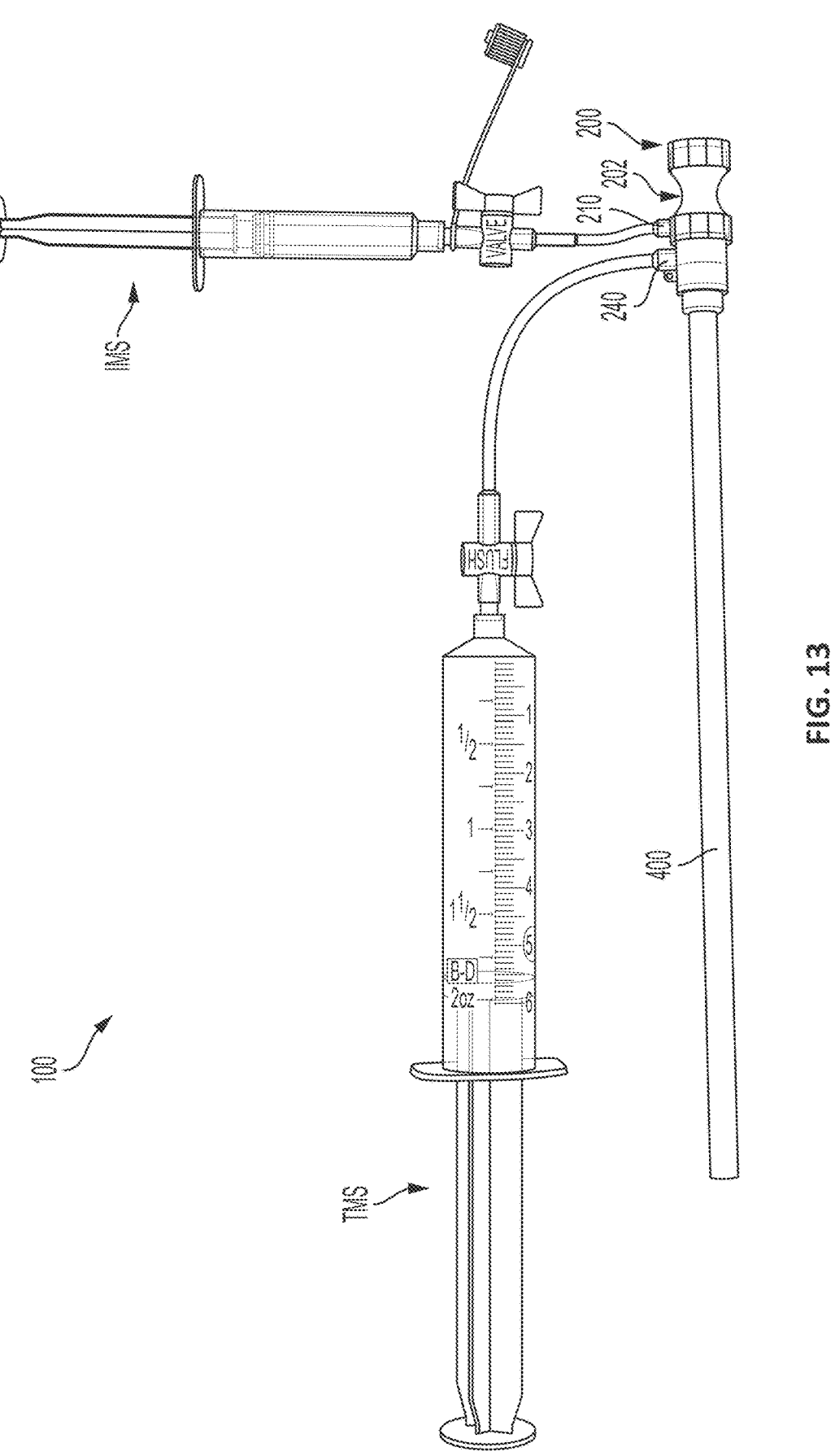
FIGS. 13 to 24 illustrate an example treatment sequence for an endoluminal device, according to some embodiments.

FIGS. 13 to 24 illustrate an example treatment sequence for an endoluminal device using the treatment system of FIG. 12A, according to some embodiments. As shown in FIG. 13, an inflation media source (IMS) and a treatment media source (TMS) are coupled to the fill port 210 and the treatment port 240 of the valve 200, respectively. The inflation media source (IMS) may be a syringe filled with inflation media (e.g., saline) for pressurizing and depressurizing the valve 200 to open and close the valve 200. The treatment media source (TMS) is optionally a syringe filled with any of the treatment media previously described.

Figure 14:
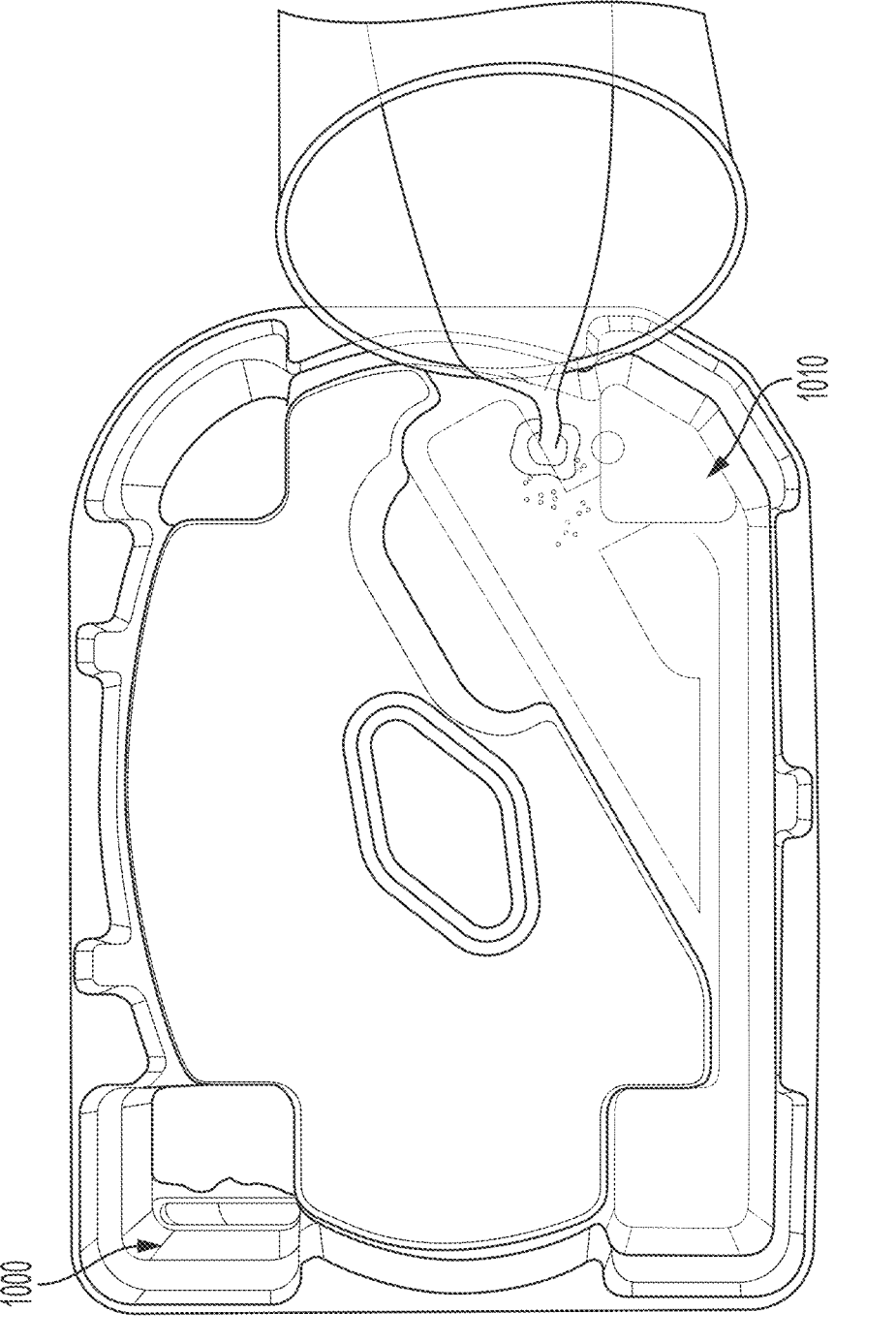

FIG. 14 shows a container 1000 (e.g., a packing tray in which the endoluminal device 600 is maintained in a sterile environment prior to use) having a pocket 1010 into which treatment media (e.g., sterile liquid) can be delivered. As shown, sterile saline is being delivered into the pocket 1010 as part of a treatment sequence.

Figure 15:
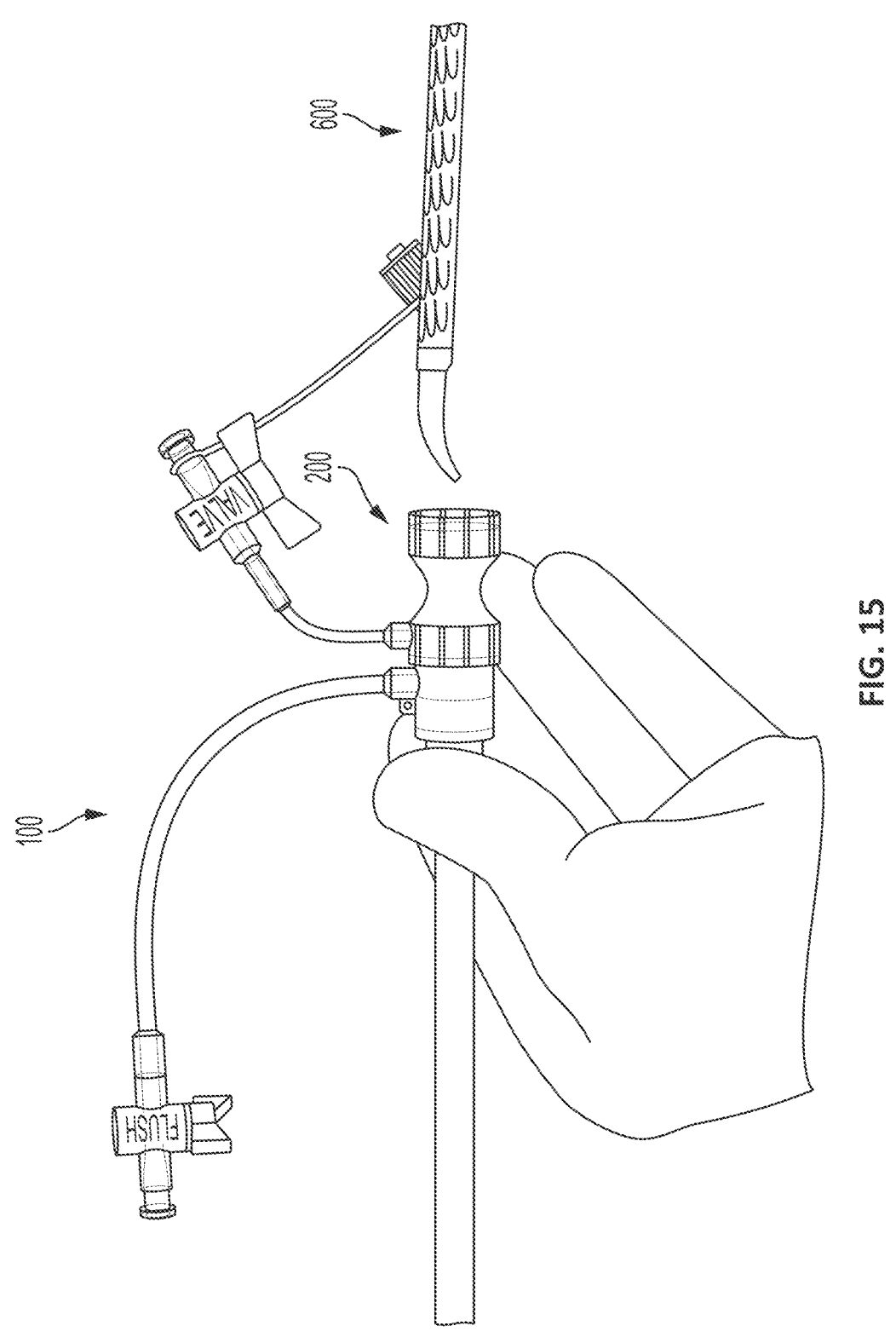

FIG. 15 shows endoluminal device 600 (e.g., in the form of a transcatheter delivery system including a catheter and an implantable device maintained at a compacted, delivery diameter or state by the delivery catheter) just prior to being introduced into the valve 200 of the treatment system 100.

Figure 16:
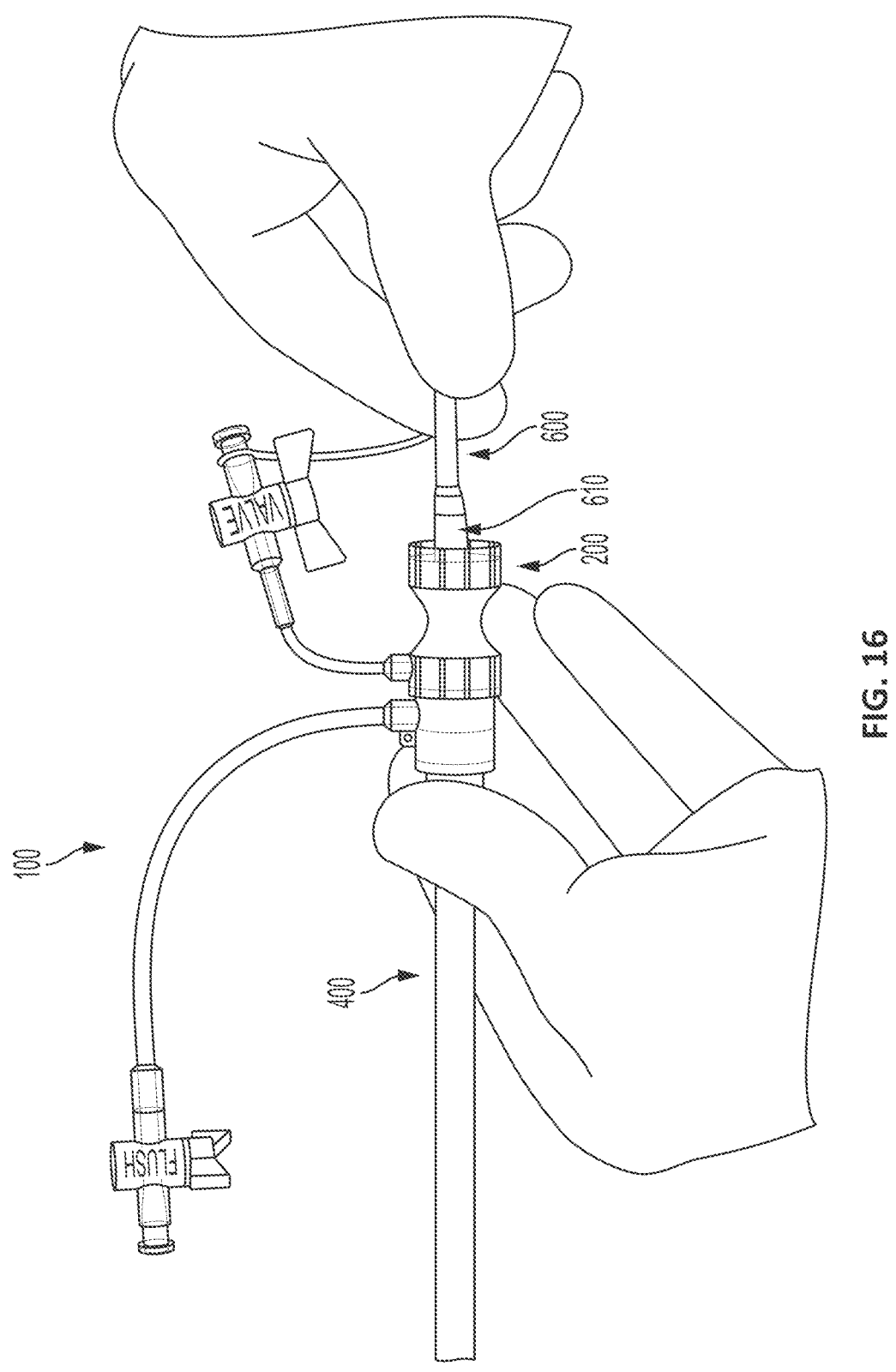

FIG. 16 shows the endoluminal device 600 introduced into the valve 200 with the implantable device 610 partially extending from the valve 200, such that a portion of the implantable device 610 is in the distal sheath 400 and a portion projects from the valve 200. The valve 200 is pressurized using the inflation media source (IMS) (FIG. 13) to transition the valve 200 to a pressurized, closed state such that the valve 200 is closed over the implantable device 610.

Figure 17:
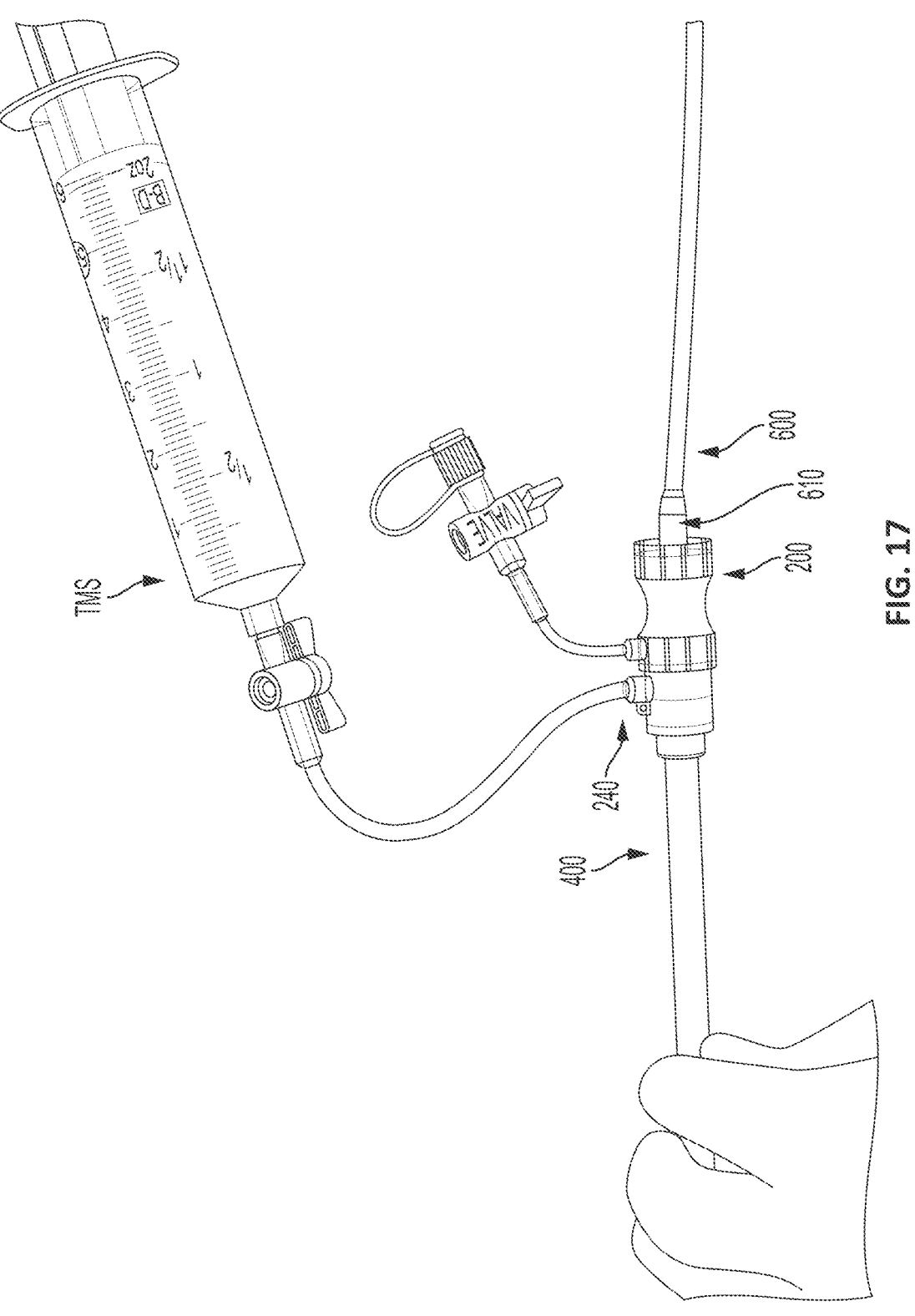
Figure 18:
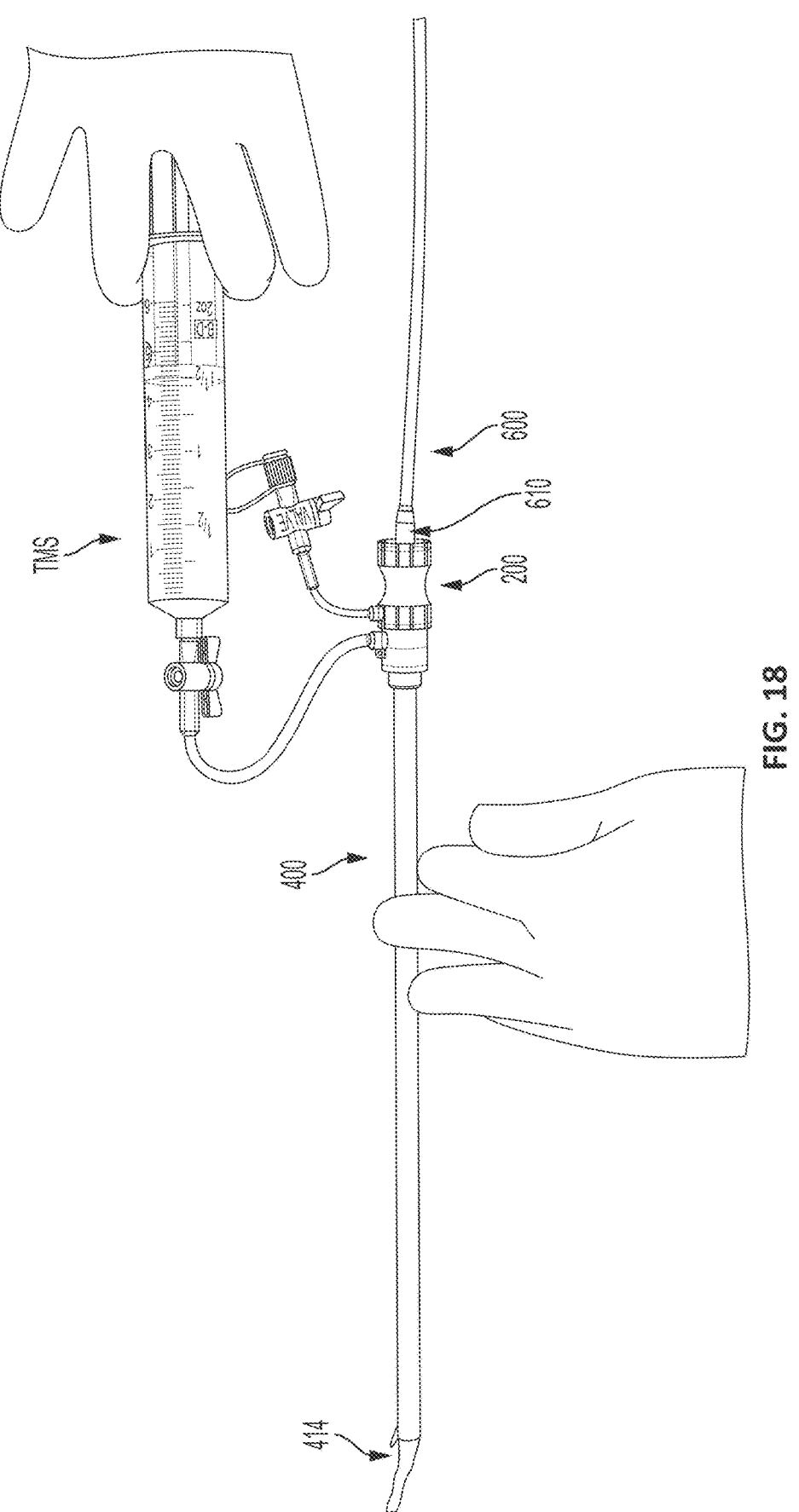

FIG. 17 shows the treatment media source (TMS) coupled to the treatment port 240 and ready to be pressurized (e.g., manually, by a user depressing the syringe plunger). FIG. 18 shows treatment media source (TMS) pressurized and the distal sheath 400 being open at the distal end 414. As show, the distal sheath 400 is being purged with treatment media passing from the distal end 414. The endoluminal device 600 may also be purged at this stage, with treatment media passing through an inner lumen (not shown) of the endoluminal device 600.

Figure 19:
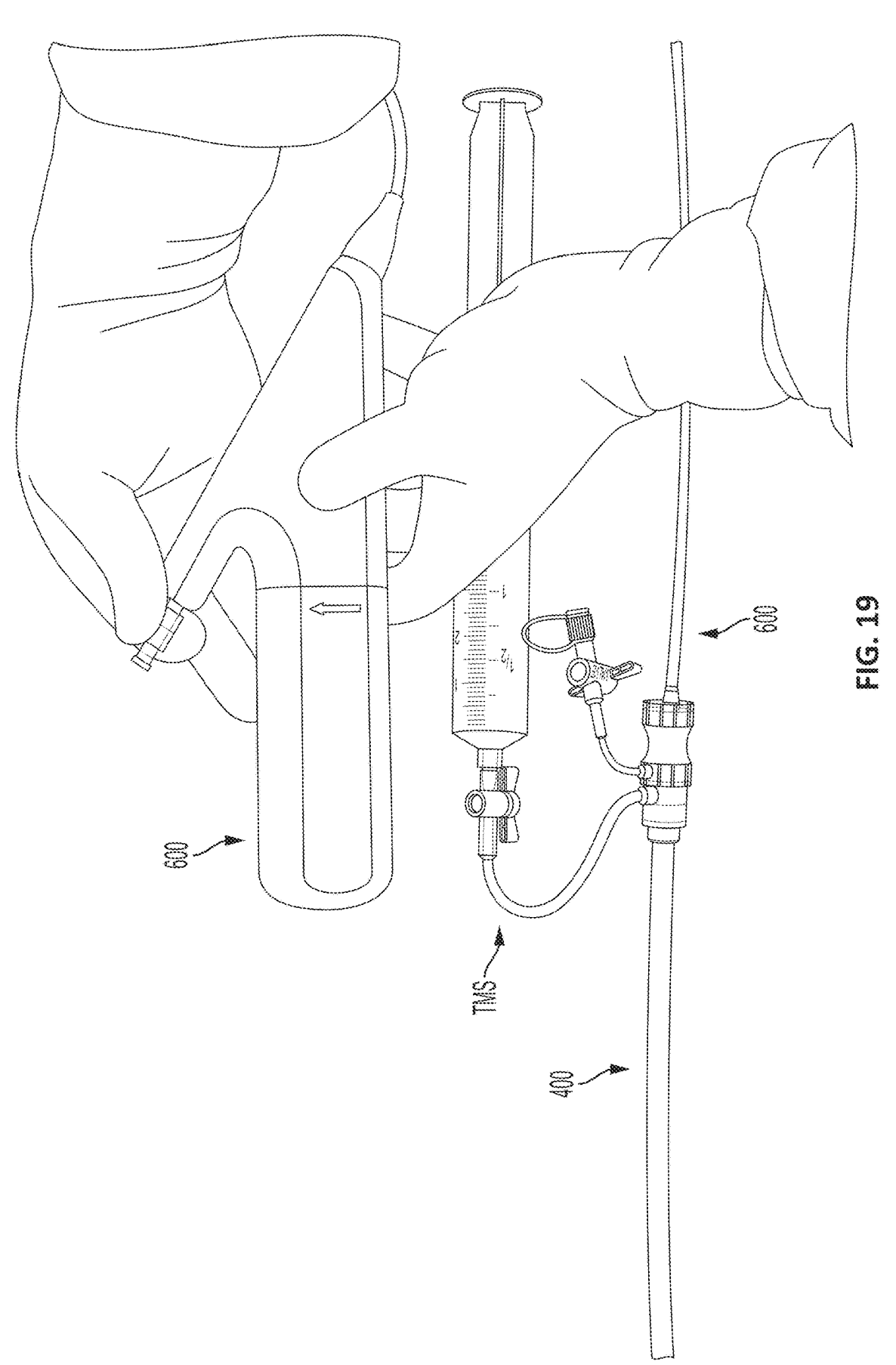

FIG. 19 shows the endoluminal device 600 being operated to seal or otherwise close an inner lumen of the endoluminal device 600 (e.g., by closing the handle portion valve (e.g., luer fitting) shown in FIG. 19).

Figure 20:
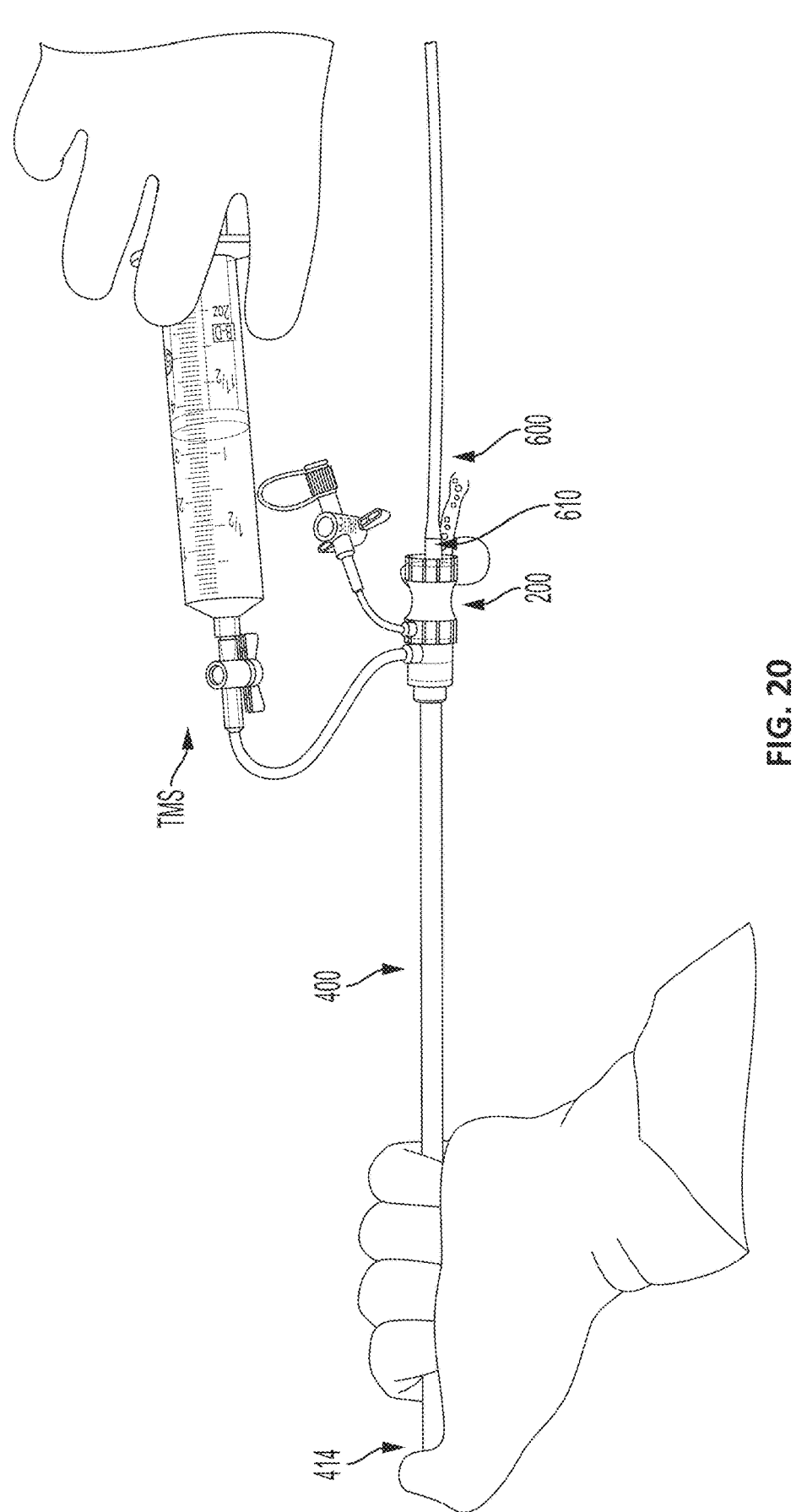
Figure 21:
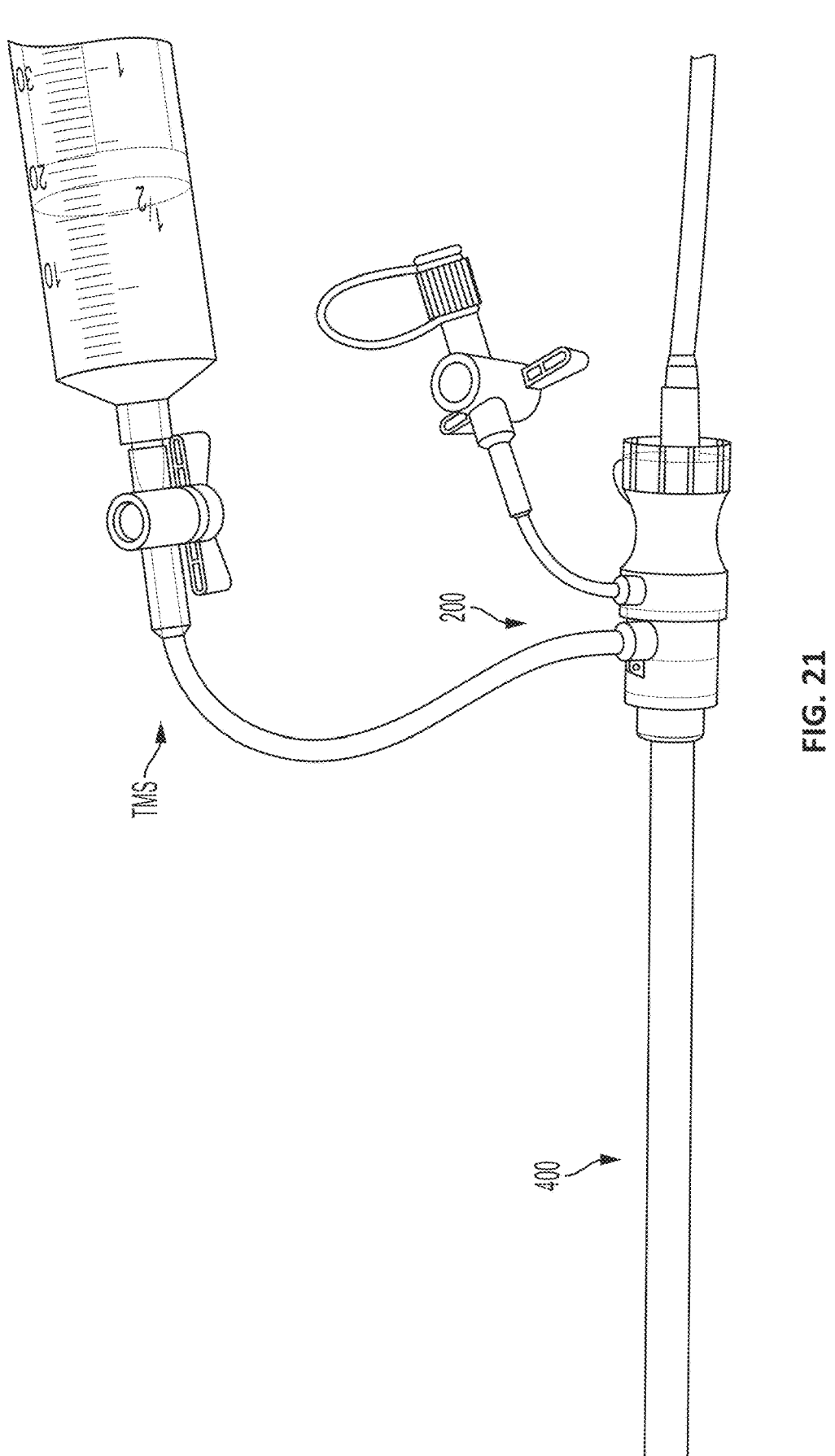

FIG. 20 shows the distal sheath 400 being sealed (e.g., with a user placing a thumb over the distal end 414) and the treatment media source (TMS) being pressurized to force treatment media into the distal sheath 400, and then past the valve 200 through the implantable device 610 (e.g., between an outer sleeve of the implantable device 610 and a body of the implantable device 610) to treat the implantable device 610 (e.g., flush air out of the implantable device 610). At this step, some treatment media may pass out through the implantable device 610 proximal to the valve 200. FIG. 21 is a closeup view around the valve 200 for additional visualization.

Figure 22:
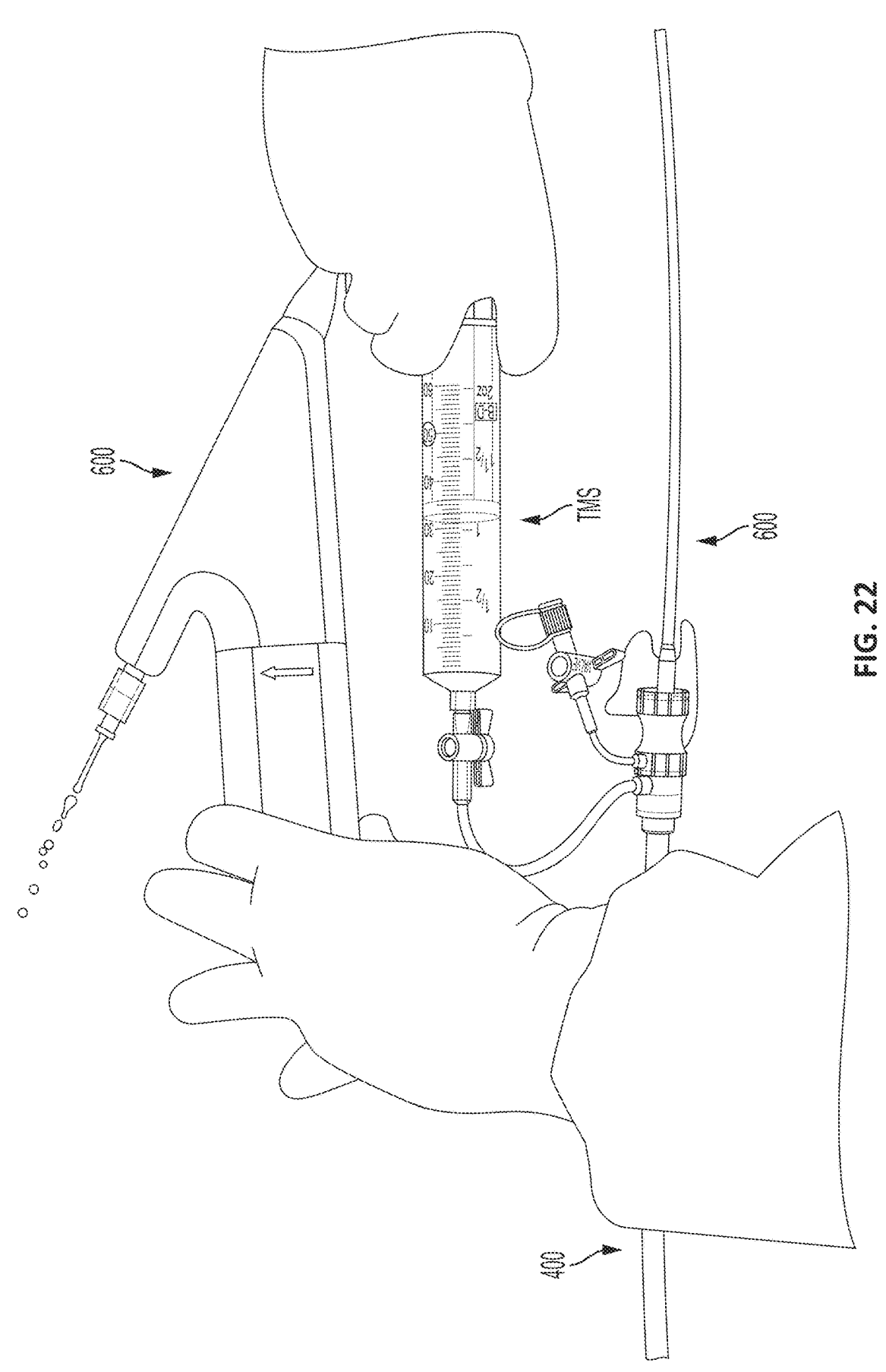

FIG. 22 shows the inner lumen of the endoluminal device 600 being flushed. For example, the handle portion valve may be opened, the treatment media source (TMS) pressurized, and treatment media may pass through the endoluminal device 600 to flush the inner lumen of the endoluminal device 600.

Figure 23:
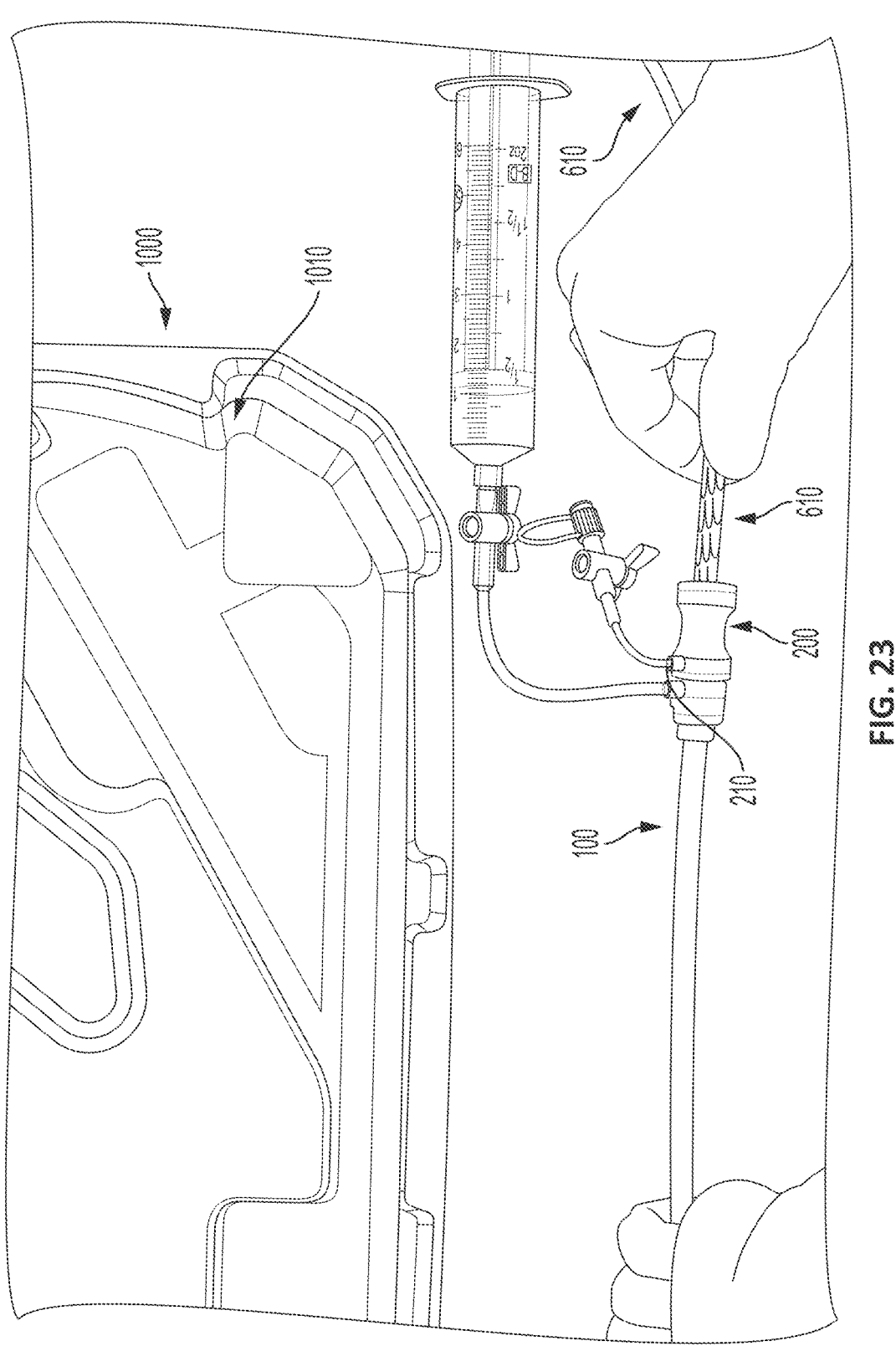
Figure 24:
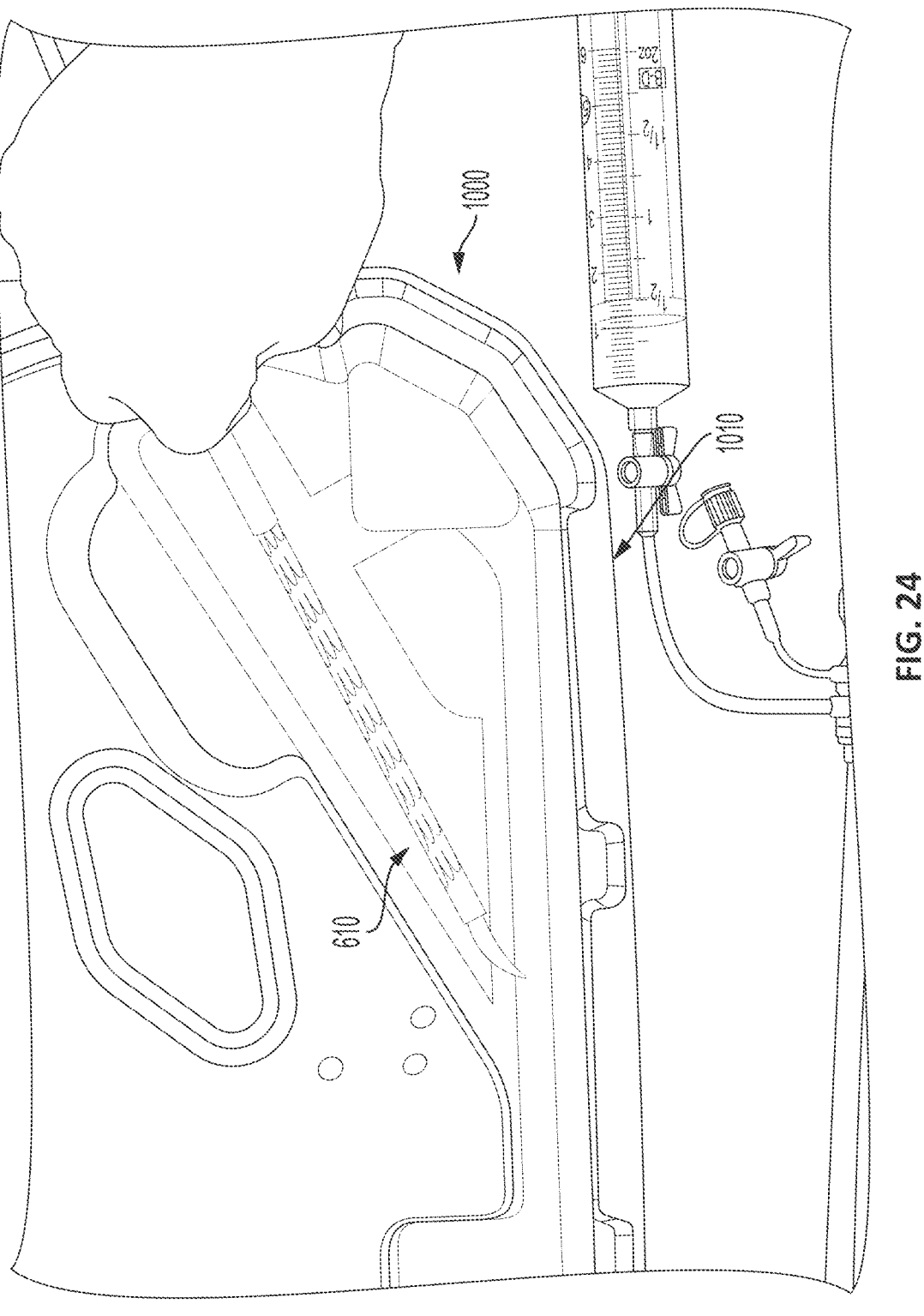

FIG. 23 shows the valve 200 being opened (e.g., by depressurizing the valve 200 using the fill port 210) and the endoluminal device 600 being removed from the treatment system 100. FIG. 24 shows the endoluminal device 600, and in particular the implantable device 610, then being placed in the pocket 1010 into which treatment media (e.g., sterile liquid) is received. In this optional step, the implantable device 610, which has now been treated, is substantially prevented from reabsorbing air. In other words, the efficacy of the treatment (e.g., the flush) is substantially preserved by placing the implantable device 610 in treatment media, such as sterile saline.

Various features have been specifically described in association with some examples and not in association with others. It is not the intent, however, to preclude the combination of features between examples. Instead, such combinations are specifically contemplated and form a part of this disclosure. The inventive concepts of this disclosure have been described both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A treatment system comprising:
an endoluminal device having a sleeve extending about a body of the endoluminal device;
a proximal valve configured to receive the endoluminal device, the proximal valve including a proximal seal mechanism actuatable between a sealed state and an unsealed state to seal around the endoluminal device;
a distal valve configured to receive the endoluminal device, the distal valve including a distal seal mechanism actuatable between a sealed state and an unsealed state around the endoluminal device;
a sheath extending distally of the distal valve; and
a treatment chamber configured to receive a treatment portion of the endoluminal device that extends between the proximal valve and the distal valve such that a sleeve maintaining the treatment portion in a compacted, delivery state extends through a portion of the proximal valve and into the treatment chamber, the treatment chamber being fluidly coupled between the proximal valve and the distal valve to define a treatment space between the proximal valve and the distal valve,
wherein the treatment system defines a length including the proximal valve, the distal valve, the sheath and the treatment chamber, the treatment system further having an inner lumen extending along the length of the treatment system, and
wherein the proximal valve is sealable about the endoluminal device such that a treatment medium exits the treatment chamber through one or more gaps between the sleeve and the body of the endoluminal device and through the proximal valve when the proximal valve is closed about the endoluminal device.

2. The system of claim 1, wherein one or both of the proximal seal mechanism and the distal seal mechanism includes an outer tube, an inner tube, and a pressurizable space formed between an inner surface of the outer tube and an outer surface of the inner tube, and the pressurizable space being pressurizable to cause the inner tube to conform around the endoluminal device to form a seal around the endoluminal device.

3. The system of claim 2, wherein the inner tube is formed of a conformable material.

4. The system of claim 3, wherein the conformable material includes one or more of ePTFE (expanded polytetrafluoroethylene), silk, and Poly-paraphenylene terephthalamide.

5. The system of claim 2, wherein the outer tube is formed of an elastomeric material.

6. The system of claim 5, wherein the elastomeric material includes silicone.

7. The system of claim 1, wherein the treatment chamber has a proximal portion adjacent to the proximal valve, a distal portion adjacent to the distal valve, the system further comprising a proximal treatment port in fluid communication with the proximal portion of the treatment chamber and a distal treatment port in fluid communication with the distal portion of the treatment chamber.

8. The system of claim 7, wherein each of the proximal and distal treatment ports includes a valve for fluidly sealing and unsealing the proximal and distal treatment portions, respectively.

9. The system of claim 1, wherein the endoluminal device is a transcatheter delivery system including a catheter and an implantable device maintained at a compacted, delivery diameter or state, and further wherein the treatment chamber is configured to receive the implantable device at the compacted, delivery diameter or state.

10. The system of claim 1, wherein the endoluminal device is a transcatheter delivery system including a catheter and an implantable device maintained at a compacted, delivery diameter or state by the delivery catheter, and further wherein the treatment chamber is configured to receive the implantable device at an intermediate, partially expanded diameter that is greater than the compacted, delivery diameter.

11. A method of treating an endoluminal device for introduction into a body of a patient, the method comprising:
positioning the endoluminal device into a treatment system, the treatment system including a proximal valve, a distal valve, and a treatment chamber defining a treatment space between the proximal valve and the distal valve, the endoluminal device including a first portion extending through the proximal valve, a second portion extending through the distal valve, and a treatment portion extending through the treatment space of the treatment chamber, wherein at least a portion of the first portion is maintained in a compacted delivery state by a sleeve, and the sleeve extends through at least a portion of the proximal valve and the proximal valve is closed over the sleeve;
closing the proximal and distal valves to seal the proximal valve against the first portion of the endoluminal device and the distal valve against the second portion of the endoluminal device; and
delivering a treatment medium into the treatment space to expose the treatment portion of the endoluminal device to the treatment medium, wherein the treatment medium exits the treatment chamber through one or more gaps between the sleeve and a body of the endoluminal device and through the proximal valve when the proximal valve is closed.

12. The method of claim 11, wherein the treatment portion of the endoluminal device includes an implantable device maintained by a delivery catheter.

13. The method of claim 12, wherein at least a portion of the second portion is maintained in the compacted delivery state by the sleeve and the distal valve is closed over the sleeve and the treatment medium exits the treatment chamber from the distal valve through one or more gaps between the sleeve and the implantable device.

14. The method of claim 11, wherein the treatment portion of the endoluminal device includes a proximal portion of an implantable device and a distal portion of the endoluminal device extends from the distal valve.

15. The method of claim 11, wherein the treatment medium is selected from one or more of saline, carbon dioxide, perfluorocarbon solution, methylene blue, and combinations thereof.

16. The method of claim 11, further comprising delivering the treatment medium into the treatment space through at least one of a proximal treatment portion in fluid communication with a proximal portion of the treatment chamber, and a distal treatment portion in fluid communication with a distal portion of the treatment chamber.

17. The method of claim 11, wherein the treatment medium exits the treatment chamber through a distal treatment port in fluid communication with a distal portion of the treatment chamber.

18. The method of claim 11, wherein the treatment system includes an introducer sheath, and the method further comprises inserting the introducer sheath into a body lumen of the patient.

19. The method of claim 18, wherein the treatment medium is delivered into the treatment space with the introducer sheath inserted into the body lumen of the patient.

20. A method of treating an endoluminal device for introduction into a body of a patient, the method comprising:
positioning the endoluminal device into a treatment system, the endoluminal device having a distal end and the treatment system including a valve and a treatment chamber extending from the valve, the endoluminal device including a first portion extending through the valve and a treatment portion extending into the treatment space of the treatment chamber, the distal end of the endoluminal device being positioned within the treatment chamber such that a sleeve maintaining at least a portion of the endoluminal device in a compacted delivery state extends through a portion of the valve and into the treatment chamber;
closing the valve to seal the valve against the first portion of the endoluminal device including the sleeve;
sealing the treatment system when the distal end of the endoluminal device is within the treatment chamber; and
delivering a treatment medium into a treatment space within the treatment chamber to expose the treatment portion of the endoluminal device to the treatment medium, wherein the treatment medium exits the treatment chamber through one or more gaps between the sleeve and a body of the endoluminal device and through the valve when the valve is closed.

21. The method of claim 20, wherein the treatment system is sealed with a cap member.

22. The method of claim 20, further comprising adjusting a length of the treatment system.

23. The method of claim 22, wherein the treatment system is sealed digitally by a user.

24. The method of claim 20, wherein a portion of the treatment medium flows in a proximal direction out from the treatment system and past the valve when the valve is sealed.

25. The method of claim 20, wherein the treatment medium flows in a proximal direction out from the treatment system through at least one folds, creases, or gaps present in the endoluminal device.

26. The method of claim 20, wherein the endoluminal device includes an implantable device and a catheter coupled to the implantable device, wherein positioning the endoluminal device includes positioning the catheter such that a first portion of the catheter extends within the treatment chamber and a second portion of the catheter extends through the valve.

27. A treatment system for an endoluminal device comprising:
a valve configured to receive at least a portion of the endoluminal device; and
a treatment chamber extending from the valve and including a treatment space containing a treatment medium, the treatment chamber configured to receive a treatment portion of the endoluminal device such that a sleeve maintaining the treatment portion in a compacted, delivery state extends through a portion of the valve and into the treatment chamber and is sealed to the valve,
wherein at least a portion of the treatment medium exits the lumen of the treatment chamber through one or more gaps between the sleeve and the endoluminal device and through the valve when the valve is closed.

* * * * *